US011236331B2

(12) United States Patent
Lewis et al.

(10) Patent No.: US 11,236,331 B2
(45) Date of Patent: Feb. 1, 2022

(54) METHODS FOR DIAGNOSING AND TREATING METASTATIC CANCER

(71) Applicant: ENTOS PHARMACEUTICALS INC., NW Edmonton (CA)

(72) Inventors: John Lewis, Edmonton (CA); Konstantin Stoletov, Edmonton (CA); Lian Willetts, Edmonton (CA)

(73) Assignee: ENTOS PHARMACEUTICALS INC., Edmonton (CA)

( * ) Notice: Subject to any disclaimer, the term of this patent is extended or adjusted under 35 U.S.C. 154(b) by 109 days.

(21) Appl. No.: 16/309,800

(22) PCT Filed: Jun. 14, 2017

(86) PCT No.: PCT/CA2017/050729
§ 371 (c)(1),
(2) Date: Dec. 13, 2018

(87) PCT Pub. No.: WO2017/214726
PCT Pub. Date: Dec. 21, 2017

(65) Prior Publication Data
US 2019/0177727 A1   Jun. 13, 2019

(30) Foreign Application Priority Data
Jun. 14, 2016   (CA) .................................. CA 2932910

(51) Int. Cl.
| *C12N 15/113* | (2010.01) |
| *A61K 31/713* | (2006.01) |
| *A61P 35/04* | (2006.01) |
| *G01N 33/574* | (2006.01) |
| *A61K 31/00* | (2006.01) |
| *A61K 33/00* | (2006.01) |
| *A61K 31/7088* | (2006.01) |
| *A61K 31/7105* | (2006.01) |
| *C07K 16/28* | (2006.01) |
| *C07K 16/44* | (2006.01) |

(52) U.S. Cl.
CPC ............ *C12N 15/113* (2013.01); *A61K 31/00* (2013.01); *A61K 31/7088* (2013.01); *A61K 31/713* (2013.01); *A61K 31/7105* (2013.01); *A61K 33/00* (2013.01); *A61P 35/04* (2018.01); *C07K 16/28* (2013.01); *C07K 16/44* (2013.01); *G01N 33/574* (2013.01); *G01N 2800/56* (2013.01)

(58) Field of Classification Search
CPC .............. C12N 15/113; C12N 15/1135; C12N 2310/14; C12N 2310/141; C12N 2310/531; C12N 2330/10; A61K 31/713; A61P 35/04
USPC ...................... 435/6.1, 91.1, 91.31, 455, 458; 514/44 A; 536/23.1, 24.5
See application file for complete search history.

(56) References Cited

U.S. PATENT DOCUMENTS

| 4,676,980 | A | 6/1987 | Segal et al. |
| 4,683,195 | A | 7/1987 | Mullis et al. |
| 4,683,202 | A | 7/1987 | Mullis |
| 4,987,071 | A | 1/1991 | Cech et al. |
| 5,093,246 | A | 3/1992 | Cech et al. |
| 5,116,742 | A | 5/1992 | Cech et al. |
| 5,328,470 | A | 7/1994 | Nabel et al. |
| 5,409,818 | A | 4/1995 | Davey et al. |
| 5,554,527 | A | 9/1996 | Fickenscher |
| 6,040,166 | A | 3/2000 | Erlich et al. |
| 2010/0152055 | A1 | 6/2010 | Kozono et al. |

FOREIGN PATENT DOCUMENTS

| CN | 101300348 A | 11/2008 |
| CN | 102388062 A | 3/2012 |
| EP | 01 320308 | 6/2003 |
| WO | WO-2007/056604 A2 | 5/2007 |
| WO | WO-2013/098797 A2 | 7/2013 |
| WO | WO 2016/002844 | 1/2016 |

OTHER PUBLICATIONS

Rudzinski et al., Fusogenic Liposomes as a Novel Nanotherapy Against Metastatic Clear Cell Renal Cell Carcinoma, J. Urology, vol. 201, No. 4S, Supplement, Poster No. MP21-15 (May 3, 2019)) (Year: 2019).*
UniProtKB—A0A024R6M5_Human, Chromosome 14 open reading frame 142, isoform CRA_a (Year: 2021).*
OriGene TrueOrf clone RC206178 in expression host HEK293T (Year: 2021).*
Bennett et al., RNA Targeting Therapeutics: Molecular Mechanisms of Antisense Oligonucleotides as a Therapeutic Platform, *Annual Review of Pharmacology and Toxicology*, 50:259-293 (2010).
Cruikshank et al., A lipidated Anti-Tat antibody enters living cells and blocks HIV-1 viral replication, *Journal of Acquired Immune Deficiency Syndromes and Human Retrovirology*. 14:193-203 (1997).
Gaynor et al., RNA interference: a chemist's perspective, *Chem. Soc. Rev.* 39:4169-84 (2010).
Gene ID: 100126317, MIR374B microRNA 374b [*Homo sapiens* (human)], dated Feb. 13, 2019).
Gene ID: 11015, KDELR3 KDEL endoplasmic reticulum protein retention receptor 3 [*Homo sapiens* (human)], dated Feb. 13, 2019.
Gene ID: 161145, TMEM229B transmembrane protein 229B [*Homo sapiens* (human)], dated Feb. 13, 2019.
Gene ID: 321, APBA2 amyloid beta precursor protein binding family A member 2 [*Homo sapiens* (human], dated Mar. 3, 2019.
Gene ID: 406906, MIR 122 microRNA 122 [*Homo sapiens* (human)], dated Mar. 19, 2019.

(Continued)

*Primary Examiner* — Jane J Zara
(74) *Attorney, Agent, or Firm* — Marshall, Gerstein & Borun LLP

(57) ABSTRACT

Disclosed are methods of diagnosing and treating metastatic cancer in a subject. The methods involve detecting or modulating the expression of at least one of Kif3b, ACTB, SRPK1, TM EM 229b, Cl4orf142, KB-1460A1.5, ACTC1, Nr2f1, KIAA0922, KDELR3, APBA2, miRNA 130b, miRNA 374b, or miRNA 122 in a biological sample from the subject.

2 Claims, 18 Drawing Sheets

(56) References Cited

OTHER PUBLICATIONS

Gene ID: 422400, TMEM131L transmembrane 131 like [*Gallus gallus* (chicken)], dated Feb. 14, 2019.
Gene ID: 6732, SPRK1 SRSF protein kinase 1 [*Homo sapiens* (human)], dated Mar. 3, 2019.
Gene ID: 70, ACTC1 actin alpha cardiac muscle 1 [*Homo sapiens* (human)], dated Mar. 3, 2019.
Gene ID: 7025, NR2F1 nuclear receptor subfamily 2 group F member 1 [*Homo sapiens* (human)], dated Feb. 13, 2019.
Gene ID: 84520, GON7 GON7 subunit of KEOPS complex [*Homo sapiens* (human)], dated Feb. 13, 2019.
Gene ID: 9371, KIF3B kinesin family member 3B [*Homo sapiens* (human)], dated Feb. 13, 2019.
Holland et al., Detection of specific polymerase chain reaction product by utilizing the 5' → 3' exonuclease activity of Thermus aquaticus DNA polymerase, *Proc. Natl. Acad. Sci. USA*. 88:7276-80(1991).
Huang, et al., Suppression of KIF3B Expression Inhibits Human Hepatocellular Carcinoma Proliferation, *Dig Dis Sci*. 59:795-806 (2014).
Hyrup et al., Peptide Nucleic Acids (PNA): Synthesis, properties and potential applications, *Bioorganic & Medicinal Chemistry*. 4(1):5-23 (1996).
Innis et al., PCR Protocols: A Guide to Methods and Applications, Academic Press, Inc., San Diego, CA (1990).
International Search Report of the International Searching Authority, for U.S. International Application No. PCT/CA2017/050729, dated Sep. 29, 2017.
International Preliminary Report on Patentability, for U.S. International Patent Application No. PCT/CA2017/050729, dated Dec. 18, 2018.
Juliano et al., The Chemistry and Biology of Oligonucleotide Conjugates, *Acc. Chem. Res*. 45(7):1067-76 (2012).
Kishimoto et al., In vivo imaging of lymph node metastasis with telomerase-specific replication-selective adenovirus, *Nature Medicine*. 12:1213-19 (2006).
Lauer et al., Drug design strategies for the treatment of prostate cancer, *Expert Opinion on Drug Discovery*. 10(1):81-90 (2015).
Li et al., Emerging therapeutic targets in metastatic progression: A focus on breast cancer, *Pharmacology & Therapeutics*. 161:79-96 (2016).
Liang et al., Distribution and cloning of eukaryotic mRNAs by means of differential display: refinements and optimization, *Nucleic Acids Research*. 21(14):3269-75 (1993).
Mehlen et al., Metastasis: a question of life or death, *Nature Reviews*. 6:449-58 (2006).
Ohara et al., One-sided polymerase chain reaction: The amplification of cDNA, *Proc. Natl. Acad. Sci. USA*. 86:5673-77 (1989).
Palmer et al., Integrin-Free Tetraspanin CD151 Can Inhibit Tumor Cell Motility upon Clustering and Is a Clinical Indicator of Prostate Cancer Progression, *Cancer Res.*, 74(1):173-187 (2014).
Rettig et al., Progress Toward In Vivo Use of siRNAs-II, *Molecular Therapy*. 20(3):483-512 (2012).
Sahai, E., Illuminating the metastatic process, *Nature Reviews*. 7:737-49 (2007).
Steeg, P.S., Targeting metastasis, *Nature Reviews*. 16:201-18 (2016).
Valastyan et al., Tumor Metastasis: Molecular Insights and Evolving Paradigms, *Cell*. 147:275-92 (2011).
Written Opinion of the International Searching Authority, for U.S. International Application No. PCT/CA2017/050729, dated Sep. 29, 2017.
Yuan et al., Recent advances of siRNA delivery by nanoparticles, *Expert Opinion on Drug Delivery*. 84(4):521-36 (2011).
Zijlstra et al., The Inhibition of Tumor Cell Intravasation and Subsequent Metastasis via Regulation of In Vivo Tumor Cell Motility by the Tetraspanin CD151, *Cancer Cell*. 13:221-34 (2008).
Minal Garg, "Targeting microRNAs in epithelial-to-mesenchymal transition-induced cancer stem cells: therapeutic approaches in cancer", Expert Opinion on Therapeutic Targets, vol. 19, No. 2, pp. 285-297 (Jan. 7, 2015).

* cited by examiner

METHODS FOR DIAGNOSING AND TREATING METASTATIC CANCER

FIELD OF THE INVENTION

Generally, the present invention is directed to cancer diagnosis and treatment. More specifically, the present invention is directed to methods for diagnosing and treating metastatic cancer in a subject.

BACKGROUND OF THE INVENTION

Metastatic dissemination is the primary cause of cancer related deaths (Mehlen and Puisieux, Nat Rev Cancer 6:449-458, 2006). While surgical resection of primary tumors in concert with systemic chemotherapy has provided success in the treatment of localized cancers, metastatic disease has proven remarkably resistant to even modern targeted therapies, rendering these cancers incurable. Indeed, to mitigate the risk of future metastasis, many patients are subjected to highly morbid treatment regimens that negatively impact quality of life (Lauer et al., Expert Opin Drug Discov 10:81-90, 2015). Ostensibly, therapies that specifically target the rate limiting steps of metastatic dissemination of tumor cells could significantly improve cancer treatment by removing the threat of systemic disease and decrease our dependency on systemic therapies with their detrimental side-effects (Steeg, Nat Rev Cancer 16:201-218, 2016; Li and Kang, Pharmacol Ther 161:79-96, 2016; Zijlstra et al., Cancer Cell 13:221-234, 2008; Mehlen and Puisieux, Nat Rev Cancer 6:449-458, 2006).

The process of metastasis is dependent on a tumour cell's ability to intravasate into the blood stream, disseminate to a distant site, evade immune detection, survive, proliferate and subsequently colonize a new microenvironment (Valastyan and Weinberg, Cell 147:275-292, 2011). Previously, it has been shown that intravasation rates are highly dependent on in vivo tumor cell motility and that when motility is inhibited using a migration-blocking antibody that targets tetraspanin CD151, both cancer cell intravasation and distant metastasis is blocked (Zijlstra et al., Cancer Cell 13:221-234, 2008; Palmer et al., Cancer Res 74:173-187, 2014). Given that the genes and signaling networks that drive in vivo motility and intravasation are different from those required for efficient primary tumor formation, identifying and interfering with these genes might prevent intravasation and metastasis. Furthermore, an improved test to detect early metastatic disease could provide a window of therapeutic opportunity prior to the full manifestation of metastasis and potentially improve overall survival for those living with advanced cancer.

SUMMARY OF THE INVENTION

According to an aspect of the present invention, there is provided a method for preventing cancer metastasis in a subject. The method involves administering an effective amount of a modulator of at least one of Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 to the subject. In one embodiment, an effective amount of an inhibitor of Kif3b, ACTB, SRPK1, TMEM229b, C14orf142, KB-1460A1.5, ACTC1, Nr2f1, KIAA0922, KDELR3, APBA2, miRNA 130b, or miRNA 374b is administered to the subject. In another embodiment, an effective amount of miRNA 122, or a compound capable of upregulating expression of miRNA 122, is administered to the subject.

According to a further aspect of the present invention, there is provided a method of detecting Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 in a patient. The method comprising: obtaining a biological sample from a human patient; detecting whether Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 is present in the sample by contacting the sample with an Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 antibody or a nucleic acid complementary to Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 mRNA and detecting binding between Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 and the antibody or hybridization between the nucleic acid complementary to Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 mRNA.

According to another aspect of the present invention, there is provided a method of diagnosing and treating cancer metastasis in a patient. The method comprising: obtaining a biological sample from a human patient; detecting whether at least one of Kif3b, ACTB, SRPK1, TMEM229b, C14orf142, KB-1460A1.5, ACTC1, Nr2f1, KIAA0922, KDELR3, APBA2, miRNA 130b, or miRNA 374b is present in the biological sample and/or miRNA 122 is absent in the biological sample; diagnosing the patient with metastatic cancer or development of metastatic cancer when the presence of Kif3b, ACTB, SRPK1, TMEM229b, C14orf142, KB-1460A1.5, ACTC1, Nr2f1, KIAA0922, KDELR3, APBA2, miRNA 130b, or miRNA 374b in the biological sample is detected and/or miRNA 122 is absent; and administering an effective amount of an inhibitor of at least one of Kif3b, ACTB, SRPK1, TMEM229b, C14orf142, KB-1460A1.5, ACTC1, Nr2f1, KIAA0922, KDELR3, APBA2, miRNA 130b, or miRNA 374b and/or an effective amount of miRNA 122, or a compound capable of upregulating expression of miRNA 122 to the diagnosed patient.

According to a further aspect of the invention, there is provided use of at least one of Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 for diagnosing metastatic cancer in a subject.

According to another aspect of the invention, there is provided use of an inhibitor of at least one of Kif3b, ACTB, SRPK1, TMEM229b, C14orf142, KB-1460A1.5, ACTC1, Nr2f1, KIAA0922, KDELR3, APBA2, miRNA 130b, or miRNA 374b and/or an effective amount of miRNA 122, or compound capable of upregulating expression of miRNA 122 for preventing cancer metastasis in a subject.

In one embodiment, the inhibitor is a gene silencing nucleic acid molecule or a small molecule. The gene silencing nucleic acid molecule being, for example, a short interfering RNA, antisense oligonucleotide, short hairpin RNA, microRNA, ribozyme or other RNA interference molecule. The small molecule being a peptide, peptoid, amino acid, amino acid analog, organic or inorganic compound.

In a further embodiment, the human patient has cancer.

In yet a further embodiment, the biological sample is a tumor biopsy.

BRIEF DESCRIPTION OF THE DRAWINGS

These and other features, aspects and advantages of the present invention will become better understood with regard to the following description and accompanying drawings wherein.

DESCRIPTION OF THE INVENTION

Figure 1:
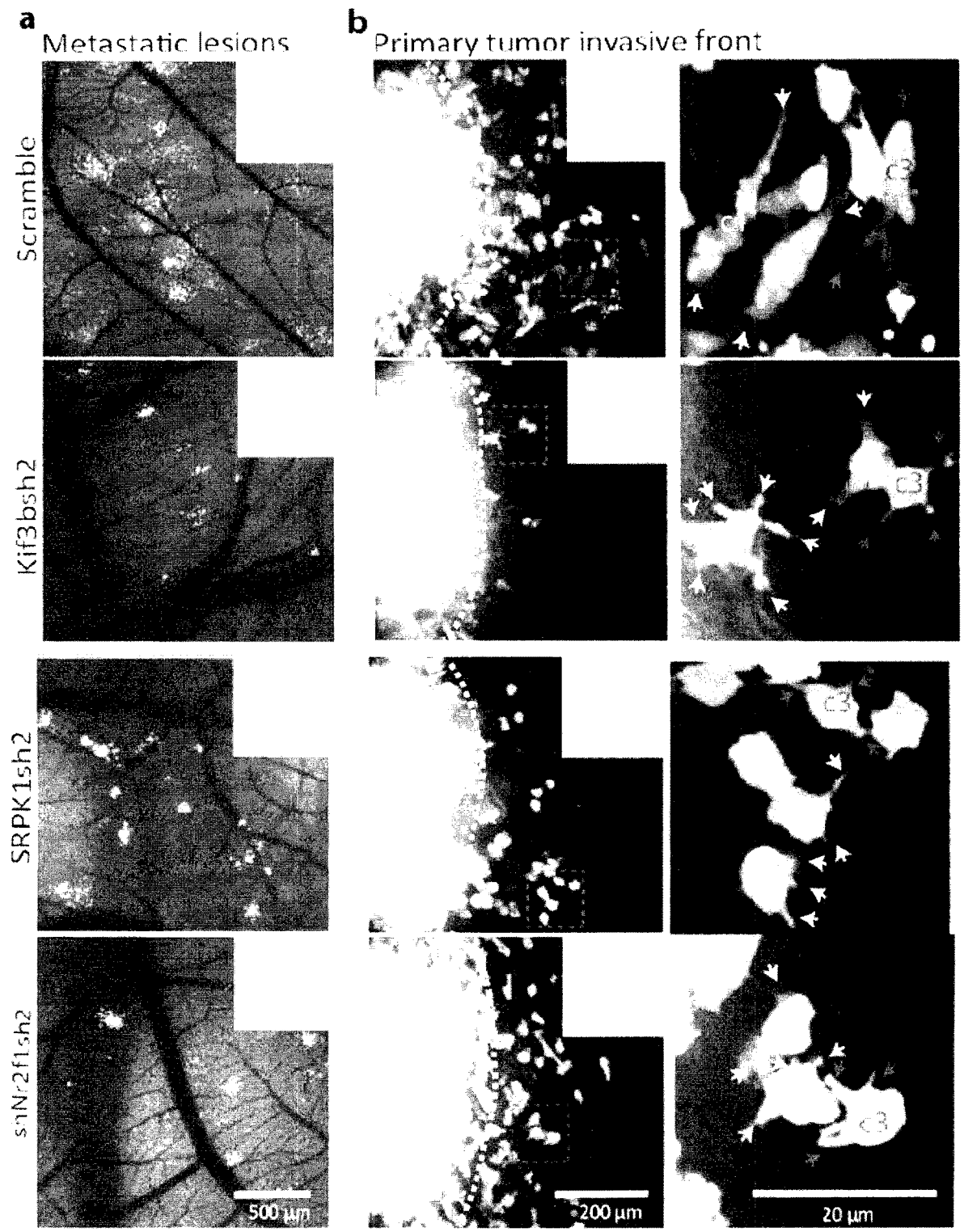
FIG. 1. is a graphical representation showing that genes identified in the screen are required for productive cancer cell invasion in vivo. a) Metastatic colonies produced by HEp3 cells transduced by scramble shRNA or shRNAs targeting Kif3b, SRPK1 or Nr2f1. Insets show representative cell tracks within the metastatic colonies. b) Left panel shows invasive fronts of primary tumors produced by HEp3 cells transduced by scramble shRNA or shRNAs targeting Kif3b, SRPK1 or Nr2f1. Insets show representative cell tracks at the invasive fronts. Right panel shows invasive cells from red dashed squares in the left panel. Color-coded arrows point to cell protrusions formed by the individual, correspondingly color coded labeled cells (c1-c3). c) Individual cell tracks velocities for control and mutant cell lines from (a). d) Individual cell tracks displacement rate (productivity) for control and mutant cell lines from (a). e) Individual cell tracks velocity for control and mutant cell lines from (b). d) Individual cell track displacement rate for control and mutant cell lines from (b). g) Number of invasive cells per field that migrated out of the primary tumors for cell lines from (b). h) Number of cell protrusion per cell for control and mutant cell lines from (b).
Figure 1:
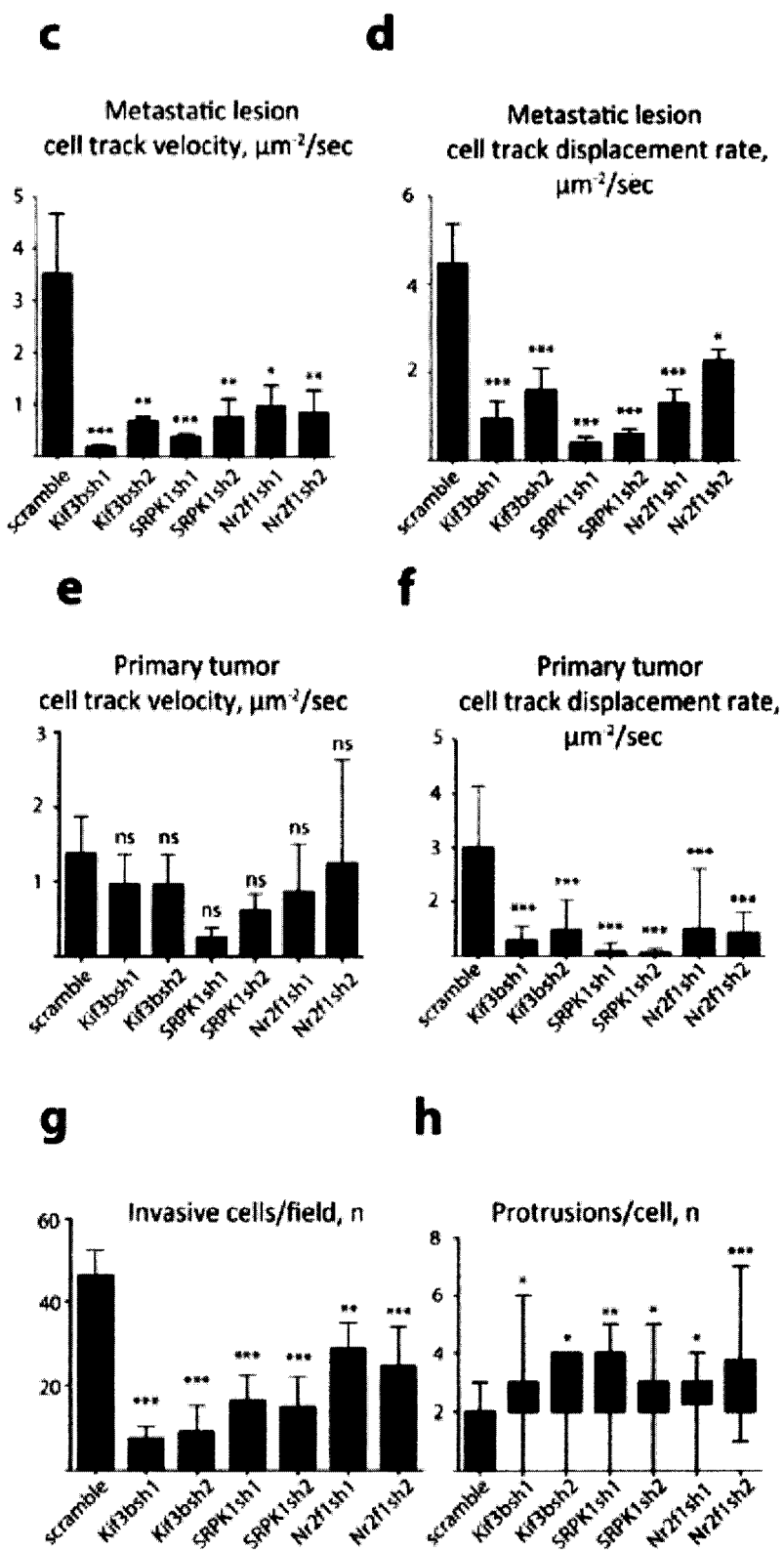

The following description is of one particular embodiment by way of example only and without limitation to the combination necessary for carrying the invention into effect.

According to an embodiment, there is provided a method for preventing metastasis in a subject having cancer. The method involves modulating the gene expression of at least one of kinesin-like protein 3b (Kif3b), serine/threonine-protein kinase 1 (SRPK1), transmembrane protein 229b (TMEM229b), chromosome 14 open reading frame 142 (C14orf142), nuclear receptor subfamily 2, group F, member 1 (Nr2f1), miRNA 130b, miRNA 374b or miRNA 122 in the cancerous tumor. In some embodiments, the method involves reducing, preventing or "silencing" expression of at least one of Kif3b, ACTB, SRPK1, TMEM229b, C14orf142, KB-1460A1.5, ACTC1, Nr2f1, KIAA0922, KDELR3, APBA2, miRNA 130b, and miRNA 374b 122 in the cancerous tumor. In other embodiments, the method involves increasing expression of miRNA 122 in the cancerous tumor.

Using the method described herein, the expression of Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 was found to be associated with cancer motility and modulating the expression of these genes prevented the cancer from spreading from a focal lesion.

For the purposes of the present discussion, the term "modulating" can mean either the upregulation of gene expression or the downregulation of gene expression when compared to a basal level of expression in the cell.

It will be understood that gene expression may refer to the production of a polypeptide from the nucleic acid sequence of a gene. Gene expression may include both transcription and translation processes, and so gene expression may refer to production of a nucleic acid sequence such as an mRNA (i.e. transcription), production of a protein (i.e. translation), or both. By way of example, a vector (either viral, plasmid, or other) comprising one or more copies of the particular gene each driven by a suitable promoter sequence (for example, a constitutive or inducible promoter), may be introduced into cells via transfection, electroporation, or viral infection, or another suitable method known in the art. Suitable expression vector techniques for introducing a particular gene into a cell are known in the art (see, for example, Molecular Cloning: A Laboratory Manual (4th Ed.), 2012, Cold Spring Harbor Laboratory Press).

As will be known to one of skill in the art, nucleotide sequences for expressing a particular gene may encode or include one or more suitable features as described in, for example, "Genes VII", Lewin, B. Oxford University Press (2000) or "Molecular Cloning: A Laboratory Manual", Sambrook et al., Cold Spring Harbor Laboratory, 3rd edition (2001). A nucleotide sequence encoding a polypeptide or protein may be incorporated into a suitable vector or expression cassette, such as a commercially available vector or expression cassette. Vectors may also be individually constructed or modified using standard molecular biology techniques, as outlined, for example, in Sambrook et al. (Cold Spring Harbor Laboratory, 3rd edition (2001)). The person of skill in the art will recognize that a vector may include nucleotide sequences encoding desired elements that may be operably linked to a nucleotide sequence encoding a polypeptide or protein. Such nucleotide sequences encoding desired elements may include suitable transcriptional promoters, transcriptional enhancers, transcriptional terminators, translational initiators, translational terminators, ribosome binding sites, 5'-untranslated region, 3'-untranslated regions, cap structure, poly A tail, and/or an origin of replication. Selection of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

Included as part of this invention are nucleic acid vectors, often expression vectors, which contain a nucleotide sequence that corresponds to the miRNA 122 gene (Gene ID: 406906) or that is complementary or at least partially complementary to nucleic acid corresponding to Kif3b (Gene ID: 9371), SRPK1 (Gene ID: 6732), TMEM229b (Gene ID: 161145), C14orf142 (Gene ID: 84520), KB-1460A1.5, ACTC1 (Gene ID: 70), Nr2f1 (Gene ID: 7025), KIAA0922 (Gene ID: 422400), KDELR3 (Gene ID: 11015), APBA2 (Gene ID: 321), miRNA 130b (Gene ID: 406920), or miRNA 374b (Gene ID: 100126317) genes. A vector is a nucleic acid molecule capable of transporting another nucleic acid to which it has been linked and can include a plasmid, cosmid, or viral vector. The vector can be capable of autonomous replication or it can integrate into a host DNA. Viral vectors may include replication defective retroviruses, adenoviruses and adeno-associated viruses for example.

The person of skill in the art will recognize that the expression of particular genes within a cell may be reduced, prevented, or "silenced" using any of a variety of well-known methods. By way of non-limiting example, gene expression may be silenced using gene silencing nucleic acids such as siRNA (short interfering RNAs), antisense oligonucleotides (AONs), short hairpin RNAs (shRNAs), microRNAs (miRNAs), or other RNA interference (RNAi) or antisense gene silencing triggers, among others (see, for example, Gaynor et al., Chem. Soc. Rev. 39: 4196-4184, 2010; Bennett et al., Annual Review of Pharmacology and Toxicology 50: 259-293, 2010). Gene expression may be decreased by other pre- or post-transcriptional gene silencing techniques known in the art. Given a particular gene sequence, the person of skill in the art will be able to design gene silencing oligonucleotides capable of targeting said gene sequence, reducing expression of the gene. Various software-based tools are available for designing siRNAs or AONs for targeting a particular gene, including those available from the Whitehead Institute or those available from commercial providers of siRNAs. For example, an siRNA antisense strand, or an antisense oligonucleotide, which is fully or substantially complementary to a region of the gene-expressed mRNA sequence may be prepared, and used for targeted gene silencing by triggering RISC or RNase H-mediated mRNA degradation. Gene silencing nucleic acids may be prepared as described in, for example, Current Protocols in Nucleic Acids Chemistry, published by Wiley.

An siRNA or RNAi is a nucleic acid that forms a double stranded RNA and has the ability to reduce or inhibit expression of a gene or target gene when the siRNA is delivered to or expressed in the same cell as the gene or target gene. siRNA is short double-stranded RNA formed by the complementary strands. Complementary portions of the siRNA that hybridize to form the double stranded molecule often have substantial or complete identity to the target molecule sequence. In one embodiment, an siRNA is a nucleic acid that has substantial or complete identity to a target gene and forms a double stranded siRNA.

When designing siRNA molecules, the targeted region often is selected from a given DNA sequence beginning 50 to 100 nucleotides downstream of the start codon. Initially, 5' or 3' UTRs and regions nearby the start codon were avoided assuming that UTR-binding proteins and/or translation initiation complexes may interfere with binding of the siRNP or RISC endonuclease complex. Sometimes regions of the target 23 nucleotides in length conforming to the sequence motif AA(N19)TT (N, an nucleotide), and regions with approximately 30% to 70% G/C-content (often about 50% G/C-content) often are selected. If no suitable sequences are found, the search often is extended using the motif NA (N2 1). The sequence of the sense siRNA sometimes corresponds to (N19) TT or N21 (position 3 to 23 of the 23-nt motif), respectively. In the latter case, the 3' end of the sense siRNA often is converted to TT. The rationale for this sequence conversion is to generate a symmetric duplex with respect to the sequence composition of the sense and antisense 3' overhangs. The antisense siRNA is synthesized as the complement to position 1 to 21 of the 23-nt motif. Because position 1 of the 23-nt motif is not recognized sequence-specifically by the antisense siRNA, the 3'-most nucleotide residue of the antisense siRNA can be chosen deliberately. However, the penultimate nucleotide of the antisense siRNA (complementary to position 2 of the 23-nt motif) often is complementary to the targeted sequence. For simplifying chemical synthesis, TT often is utilized. siRNAs corresponding to the target motif NAR (N17)YNN, where R is purine (A,G) and Y is pyrimidine (C,U), often are selected. Respective 21 nucleotide sense and antisense siRNAs often begin with a purine nucleotide and can also be expressed from pol III expression vectors without a change in targeting site. Expression of RNAs from pol III promoters can be more efficient when the first transcribed nucleotide is a purine.

The sequence of the siRNA can correspond to the full length target gene, or a subsequence thereof. Often, the siRNA is about 15 to about 50 nucleotides in length (e.g., each complementary sequence of the double stranded siRNA is 15 to 50 nucleotides in length, and the double stranded siRNA is about 15 to 50 base pairs in length, sometimes about 20 to 30 nucleotides in length or about 20 to 25 nucleotides in length, e.g., 20, 21, 22, 23, 24, 25, 26, 27, 28, 29, or 30 nucleotides in length. The siRNA sometimes is about 21 nucleotides in length. Methods of using siRNA are known in the art, and specific siRNA molecules may be purchased from a number of companies including Dharmacon Research, Inc.

Gene expression may be inhibited by the introduction of double-stranded RNA (dsRNA), which induces potent and specific gene silencing, a phenomenon called RNA interference or RNAi. See, e.g., Fire et al., U.S. Pat. No. 6,506,559; Tuschl et al., PCT International Publication No. WO 01/75164; Kay et al., PCT International Publication No. WO 03/010180A1). This process has been improved by decreasing the size of the double-stranded RNA to 20-24 base pairs (to create small-interfering RNAs or siRNAs) that switched off genes in mammalian cells without initiating an acute phase response, i.e., a host defense mechanism that often results in cell death. There is increasing evidence of post-transcriptional gene silencing by RNA interference (RNAi) for inhibiting targeted expression in mammalian cells at the mRNA level, in human cells. There is additional evidence of effective methods for inhibiting the proliferation and migration of tumor cells in human patients, and for inhibiting metastatic cancer.

In another embodiment, the gene silencing nucleic acid is a ribozyme. A ribozyme having specificity for a target nucleotide sequence can include one or more sequences complementary to such a nucleotide sequence, and a sequence having a known catalytic region responsible for mRNA cleavage (see, e.g. U.S. Pat. No. 5,093,246). For example, a derivative of a Tetrahymena L-19 IVS RNA is sometimes utilized in which the nucleotide sequence of the active site is complementary to the nucleotide sequence to be cleaved in a mRNA (see, e.g., Cech et al., U.S. Pat. No. 4,987,071; and Cech et al., U.S. Pat. No. 5,116,742). Also, target mRNA sequences can be used to select a catalytic RNA having a specific ribonuclease activity from a pool of RNA molecules.

Gene silencing nucleic acid molecules, such as antisense, ribozyme, RNAi and siRNA nucleic acids, can be altered to form modified nucleic acid molecules. The nucleic acids can be altered at base moieties, sugar moieties or phosphate backbone moieties to improve stability, hybridization, or solubility of the molecule. For example, the deoxyribose phosphate backbone of nucleic acid molecules can be modified to generate peptide nucleic acids (see Hyrup et al., Bioorganic & Medicinal Chemistry 4 (1): 5-23, 1996). A peptide nucleic acid, or PNA, refers to a nucleic acid mimic such as a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. Synthesis of PNA oligomers can be performed using standard solid phase peptide synthesis protocols as described, for example, in Hyrup et al.

PNA nucleic acids can be used in the prognostic, diagnostic, and therapeutic applications described herein. For example, PNAs can be used as anti-sense or anti-gene agents for sequence-specific modulation of gene expression by, for example, inducing transcription or translation arrest or inhibiting replication. PNA nucleic acid molecules can also be used in the analysis of SNPs in a gene, (e.g., by PNA-directed PCR clamping); as artificial restriction enzymes when used in combination with other enzymes, (e.g., S1 nucleases (Hyrup et al., supra) or as probes or primers for DNA sequencing or hybridization (Hyrup et al., supra).

In some embodiments, the gene of interest, such as miRNA 122, will be overexpressed compared to a basal level in the cancerous tumor to minimize the possibility of the cancer metastasizing. Overexpression of a gene can be accomplished in a number of different ways, such as, but not limited to, transfecting cells/tissue with a gene construct that overexpresses the gene of interest. In addition, transfecting cells/tissue with gene constructs that influence the transcriptional or translational machinery of a gene/cell can also be used to cause overexpression of the gene of interest. Furthermore, small molecules can be developed that cause the expression of the gene of interest to be increased in cancerous cells.

Introduction of a gene, in the context of inserting a nucleic acid sequence into a cell, refers to "transfection", "transformation", or "transduction", and includes the incorporation or introduction of a nucleic acid sequence into a eukaryotic cell where the nucleic acid sequence may optionally be incorporated into the genome of the cell, or transiently expressed (for example, transfected mRNA). A protein or enzyme may be introduced into a cell by delivering the protein or enzyme itself into the cell, or by expressing an mRNA encoding the protein or enzyme within the cell, leading to its translation.

Gene silencing nucleic acid molecules may be introduced into cells using any of a number of well-known methods. Expression vectors (either viral, plasmid, or other) may be transfected, electroporated, or otherwise introduced into cells, which may then express the gene silencing nucleotide(s). Alternatively, gene silencing nucleotides themselves may be directly introduced into cells, for example via transfection or electroporation (i.e. using a transfection reagent such as but not limited to Lipofectamine™, Oligofectamine, or any other suitable delivery agent known in the art), or via targeted gene or nucleic acid delivery vehicles known in the art. Many delivery vehicles and/or agents are well-known in the art, several of which are commercially available. Delivery strategies for gene silencing nucleic acids are described in, for example, Yuan et al., Expert Opin. Drug Deliv. 8:521-536, 2011; Juliano et al., Acc. Chem. Res. 45: 1067-1076, 2012; and Rettig et al., Mol. Ther. 20:483-512, 2012. Examples of transfection methods are described in, for example, Ausubel et al., (1994) Current Protocols in Molecular Biology, John Wiley & Sons, New York. Expression vector examples are described in, for example, Cloning Vectors: A Laboratory Manual (Pouwels et al., 1985, Supp. 1987).

The skilled person will understand that antibodies, or antibody fragments, targeting one or more of the amino acids, nucleic acids, proteins, or enzymes described herein, such as monoclonal or polyclonal antibodies or Fab fragments thereof, may be generated for targeting a particular amino acid, nucleic acid, protein or enzyme target using standard laboratory techniques and thus silencing the gene. By way of non-limiting example, monoclonal antibodies to a particular target may be prepared using a hybridoma technique (see, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas pp 563-681 (Elsevier, N.Y., 1981)). The person of skill in the art will be aware of methods and techniques for preparing antibodies for a particular amino acid, protein, nucleic acid, or enzyme target. Such antibodies may be used to bind an amino acid, protein, nucleic acid, or enzyme target, preventing it from performing its regular function, resulting in a similar outcome to that arising from gene silencing of the same amino acid, nucleic acid, protein or enzyme. Therefore, in certain embodiments, antibodies may be used in place of gene silencing nucleic acids for targeting or "silencing" a particular gene.

A compound that inhibits the activity of Kif3b, ACTB, SRPK1, TMEM229b, C14orf142, KB-1460A1.5, ACTC1, Nr2f1, KIAA0922, KDELR3, APBA2, miRNA 130b, or miRNA 374b may be useful in the present invention and can include small molecules. Small molecules include, but are not limited to, peptides, peptidomimetics (e.g. peptoids), amino acids, amino acid analogs, organic or inorganic compounds (i.e. including heterorganic or organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It will be understood that compounds and/or compositions comprising or consisting of one or more of the nucleic acid and/or polypeptides as described herein may be used. Compositions may additionally comprise one or more pharmaceutically acceptable diluents, carriers, excipients, or buffers. Compositions may be used for administering one or more nucleic acids and/or polypeptides to a cell in vitro or in vivo.

When utilized as therapeutics, gene silencing nucleic acid molecules typically are administered to a subject (e.g. by direct injection at a tissue site) or generated in situ such that they hybridize with or bind to cellular mRNA and/or genomic DNA encoding a polypeptide, such as Kif3b, ACTB, SRPK1, TMEM229b, C14orf142, KB-1460A1.5, ACTC1, Nr2f1, KIAA0922, KDELR3, APBA2, miRNA 130b, or miRNA 374b, and thereby inhibit expression of the polypeptide, for example, by inhibiting transcription and/or translation. Alternatively, genes silencing nucleic acid molecules can be modified to target selected cells and then are administered systemically. For systemic administration, gene silencing nucleic acid molecules can be modified such that they specifically bind to receptors or antigens expressed on a selected cell surface, for example, by linking gene silencing nucleic acid molecules to peptides or antibodies which bind to cell surface receptors or antigens. Gene silencing nucleic acid molecules can also be delivered to cells using vectors. Sufficient intracellular concentrations of gene silencing nucleic acid molecules are achieved by incorporating a strong promoter, such as a pol II or pol III promoter, in the vector construct.

As defined herein, a therapeutically effective amount of protein or polypeptide (i.e., an effective dosage) ranges from about 0.001 to 30 mg/kg body weight, sometimes about 0.01 to 25 mg/kg body weight, often about 0.1 to 20 mg/kg body weight, and more often about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, sometimes between 2 to 8 weeks, often between about 3 to 7 weeks, and more often for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, can include a series of treatments.

For antibodies, a dosage of 0.1 mg/kg of body weight (generally 10 mg/kg to 20 mg/kg) is often utilized. If the antibody is to act in the brain, a dosage of 50 mg/kg to 100 mg/kg is often appropriate. Generally, partially human antibodies and fully human antibodies have a longer half-life within the human body than other antibodies. Accordingly, lower dosage and less frequent administration is often possible. Modifications such as lipidation can be used to stabilize antibodies and to enhance uptake and tissue penetration (e.g., into the brain). A method for lipidation of antibodies is described by Cruikshank et al. (Cruikshank et al., 1997).

Antibody conjugates can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a polypeptide such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676,980.

For compounds, exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

With regard to nucleic acid formulations, gene therapy vectors can be delivered to a subject by, for example, intravenous injection, local administration (see, e.g., U.S. Pat. No. 5,328,470) or by stereotactic injection (Chen et al., 1994). Pharmaceutical preparations of gene therapy vectors can include a gene therapy vector in an acceptable diluent, or can comprise a slow release matrix in which the gene delivery vehicle is imbedded. Alternatively, where the complete gene delivery vector can be produced intact from recombinant cells (e.g., retroviral vectors) the pharmaceutical preparation can include one or more cells which produce the gene delivery system. Examples of gene delivery vectors are described herein.

In another embodiment, the expression of at least one of Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 are used to detect whether the cancer is capable of metastasis. In this case, a biological sample is taken from the patient having the cancer and this sample is analysed to detect whether the levels of Kif3b, ACTB, SRPK1, TMEM229b, C14orf142, KB-1460A1.5, ACTC1, Nr2f1, KIAA0922, KDELR3, APBA2, miRNA 130b, or miRNA 374b are increased over a normal basal or, in the case of miRNA 122, decreased over a normal basal level in the biological sample. To determine mRNA levels, nucleic acid is isolated from a biological sample obtained from a subject. For example, nucleic acid can be isolated from blood, saliva, sputum, urine, cell scrapings, and biopsy tissue. The nucleic acid sample can be isolated from a biological sample using standard techniques. The nucleic acid sample may be isolated from the subject and then directly utilized in a method or, alternatively, the sample may be isolated and then stored (e.g. frozen) for a period of time before being subjected to analysis.

It will be appreciated that the diagnostic methods may involve determination of the expression levels of at least one of Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 using any suitable method, including, but not limited to, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR (RT-PCT), anchored PCR, competitive PCR (see, for example, U.S. Pat. No. rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276¬7280), differential display (see, for example, Liang et al., Nucl. Acid. Res., 1993, 21: 3269¬3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

In other cases, the expression of Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 may be detected at the protein level by a variety of techniques, including, but not limited to, immunoblotting, immunoprecipitation, and enzyme-linked immunosorbent assay (ELISA). Accordingly, contacting a polypeptide or protein encoded by a nucleotide sequence from a subject with an antibody that specifically binds to an epitope associated with Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 can be used to determine whether an individual has or is susceptible to developing metastatic cancer. Cells suitable for diagnosis may be obtained from a patient's blood, urine, saliva, tissue biopsy and autopsy material.

In another embodiment, the components needed to implement the method are provided as part of a kit. In particular, the kit comprises a molecule that binds to a Kif3b, ACTB, SRPK1, TMEM229b, C14orf142, KB-1460A1.5, ACTC1, Nr2f1, KIAA0922, KDELR3, APBA2, miRNA 130b, miRNA 374b, or miRNA 122 and any buffers needed to run the assay. The molecule being an a gene silencing nucleic acid molecule, small molecule or biologic that downregulates the expression or function of Kif3b, ACTB, SRPK1, TMEM229b, C14orf142, KB-1460A1.5, ACTC1, Nr2f1, KIAA0922, KDELR3, APBA2, miRNA 130b, or miRNA 374b and/or a small molecule or gene construct that is capable of upregulating the expression of miRNA 122. Optionally, the kit can include a set of instructions for use of the molecule in the assay. However, it is envisioned that the instructions need not be a set of paper instructions, instead the instructions can be provided through a URL address or QR code.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

The following Examples are provided for illustrative purposes intended for the person of skill in the art. It will be understood that these examples are intended to be non-limiting, and that a number of variations and modifications as will be known to the person of skill in the art having regard to the teachings herein may be possible.

EXAMPLES

Previously, the identification of genes required for in vivo cell motility has been impeded by the inherent difficulty in visualizing the formation of metastatic lesions in vivo (Sahai, Nat Rev Cancer 7:737-749, 2007, Kishimoto et al., Nat Med 12:1213-1219, 2006). To address this, an intravital imaging approach was used in shell-less, ex ovo avian embryos to perform a shRNA screen for gene products that regulate tumor cell motility in vivo. After intravenous injection, cancer cells disseminate widely throughout the vasculature of the embryo. A substantial fraction of these cancer cells arrest as single cells in the chorioallantoic membrane (CAM), where they undergo extravasation into the extravascular stroma and proliferate into invasive metastatic colonies. These colonies, each derived from a single cancer cell, reach the size of ~1 mm$^2$ (50-100 cells per colony) over 4 days and can be easily visualized using intravital microscopy. Because thousands of individual metastatic colonies can be simultaneously visualized in the CAM of a single embryo, it is feasible to screen large libraries of genes using this approach. Identifying motility phenotypes is straightforward. When highly motile cancer cells such as the human head and neck HEp3 cell line are injected, the resulting colonies adopt a "spread out" migratory phenotype where the proliferating cells have migrated a significant distance from the extravasation point. When the in vivo motility of tumor cells is diminished, such as that observed when using the CD151-specific migration-blocking antibody, metastatic colonies exhibit a highly compact morphology that is easily distinguished from the highly motile phenotype. These compact metastatic lesions, comprised of tightly packed cancer cells, can be readily excised from the surrounding tissue and subjected to further analysis. As had previously been seen with the targeting of CD151, the inhibition of genes required for in vivo cell motility should lead to compact colony phenotypes, allowing for the utilization of this approach to screen for therapeutic targets of cell motility that would in turn impact intravasation and metastasis.

To perform the screen, HEp3 cells were transduced with a human shRNAGIPZ microRNA-adapted shRNA lentiviral library (Open Biosystems) built using a native miR-30 primary transcript to enable processing by the endogenous RNAi pathway. This library contains 79,805 sequence-verified shRNAs targeting 30,728 human genes contained in 7 pools, along with TurboGFP to monitor successful transduction. Each pool was used to transduce HEp3 cells in culture at an MOI (0.2), favoring a single shRNA integration per cancer cell according to Poisson Distribution. When 25,000 tumour cells are injected intravenously into the avian embryo, roughly 10% of the cells arrest and extravasate in the easily accessible and visible CAM organ to form isolated metastatic colonies. To ensure 3× coverage of the 79805 shRNA clones with 99% confidence, the screen was performed in 100 embryos. Transduced GFP-expressing cells were injected intravenously into embryos in ex ovo culture at developmental day 10. On developmental day 15, the more than 200,000 colonies in the CAMs of these 100 embryos were surveyed using intravital microscopy. Of these, 67 morphologically compact metastatic lesions were identified and excised. These colonies were dissociated and cultured under selection, and 50 clones were successfully expanded in culture.

To identify the integrated shRNA, inserts from each clone were amplified by PCR using common flanking primers and resulting cDNA sequences were determined by deep sequencing on an Illumina platform. Raw sequence reads were subjected to a stringent filtering algorithm to identify the flanking miRNA sequences and exclude reads with inconsistent loop sequences and stem base-pair mismatches. Filtered sequences were then subjected to BLAST analysis against both the library and the human nucleotide (nt) database and ranked according to their abundance. Seventeen of the 50 isolated clones contained a single shRNA, while the remaining 33 clones each contained more than one shRNA.

Figure 3:
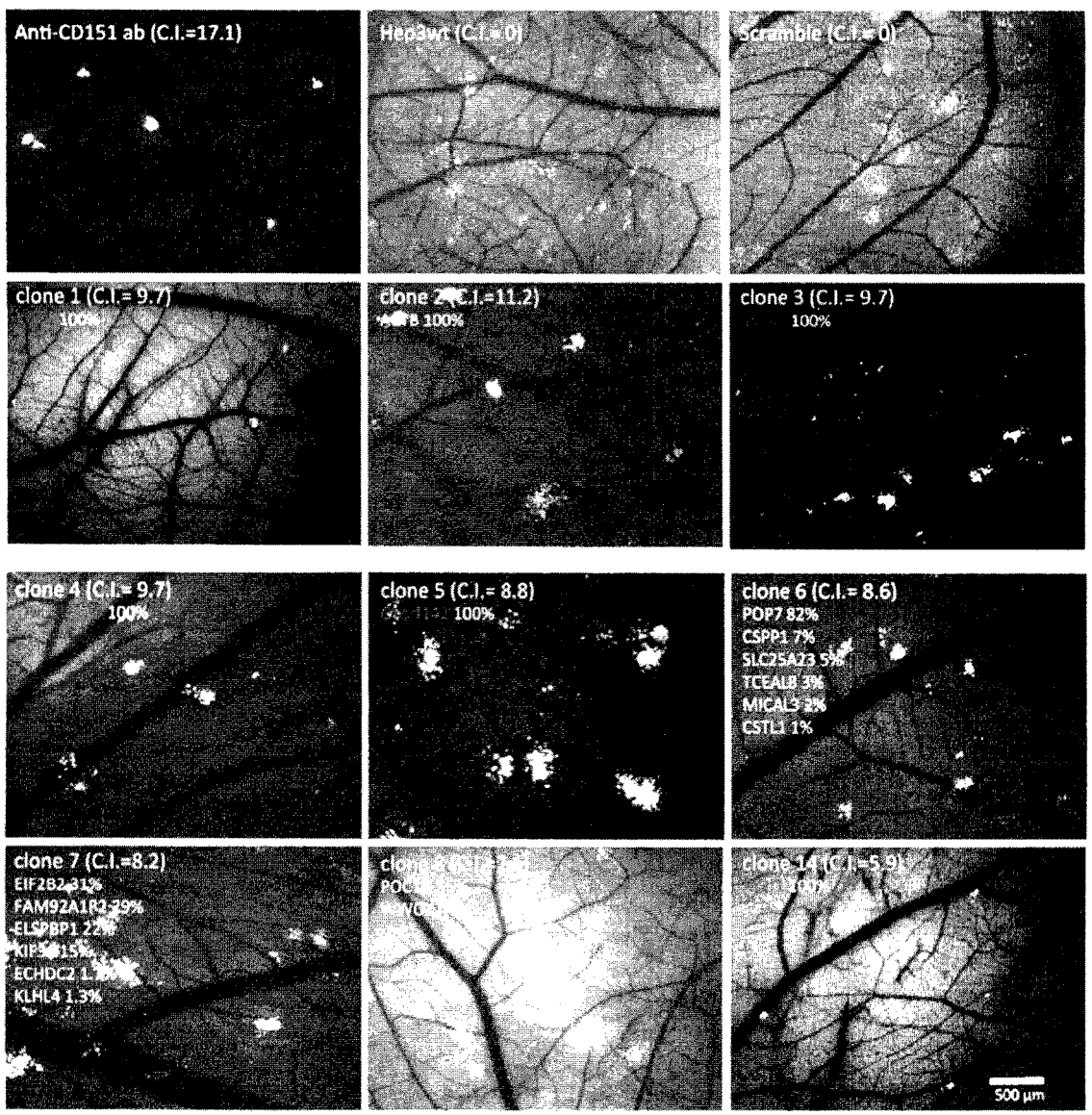
FIG. 3. is a graphical representation showing quantitative validation of the screen identified clones via re-injection. a) Representative images of compact colony forming clones isolated in the screen. Insets show the composite C.I. scores and shRNAs present in the clone, sorted by their abundance. Representative colonies formed by original (wt) and scramble shRNA transduced HEp3 cells are also shown. shRNAs selected for further analysis are highlighted in red; b) Linear Index distribution of clones identified in the screen; c) Density Index distribution of clones identified in the screen; and d) Area Index distribution of clones identified in the screen.
Figure 3:
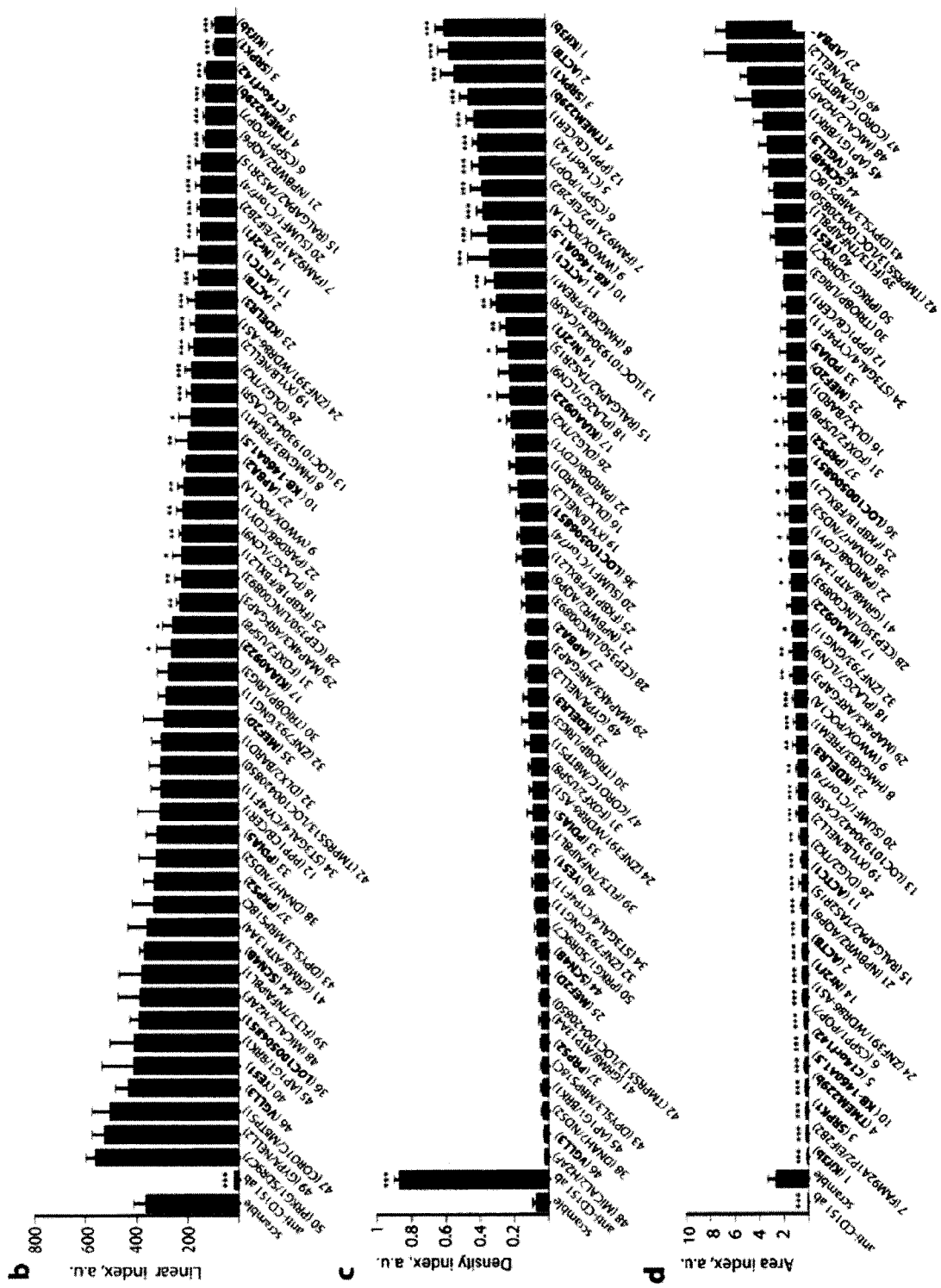
Figure 4:
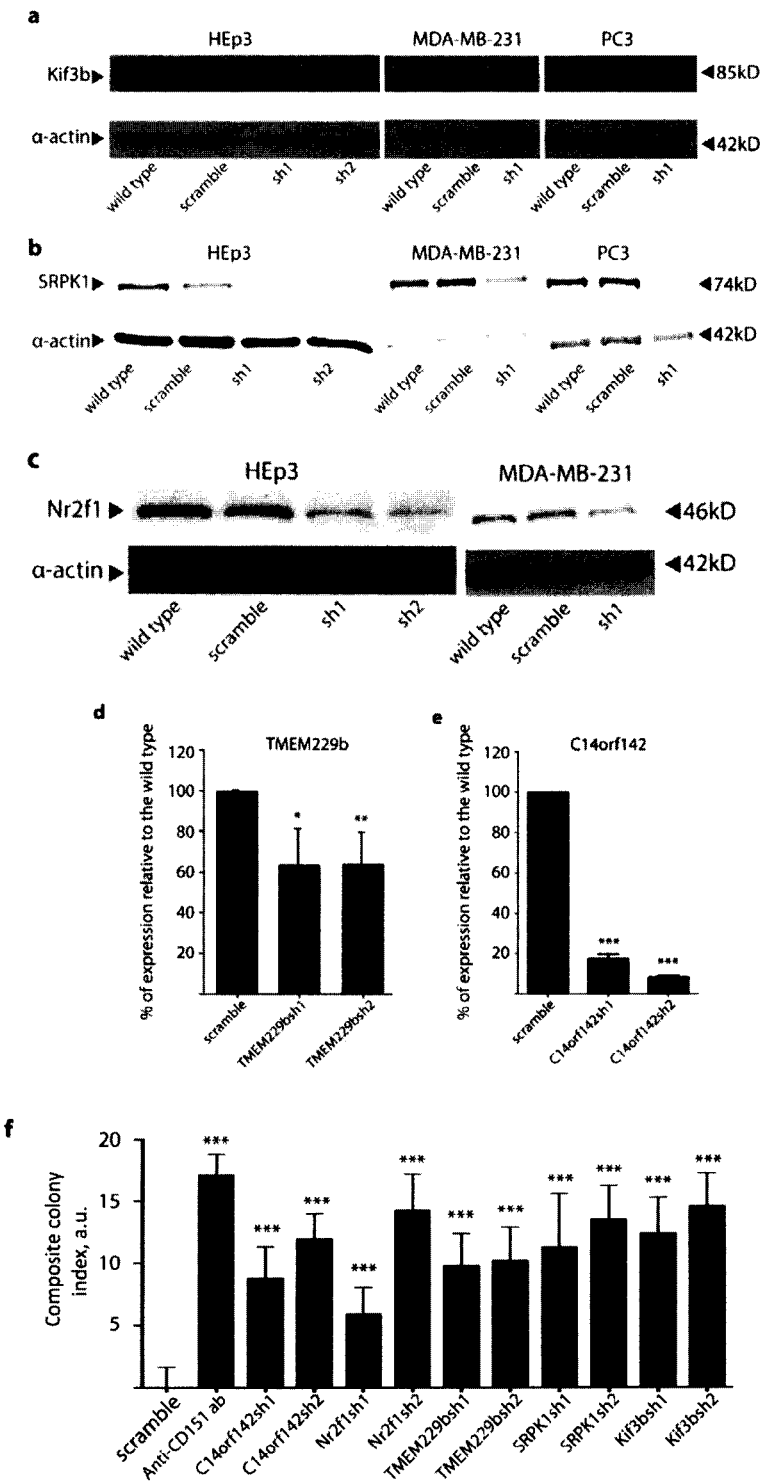
FIG. 4. is a graphical representation showing generation of mutant cell lines knockdown by expression of the screen identified genes. a) Western blotting analysis of Kif3b mutant and control cell lines (HEp3, MDA-MB-231 and PC3). b) Western blotting analysis of SRPK1 mutant and control cell lines (HEp3, MDA-MB-231 and PC3). c) Western blotting analysis of Nr2f1 mutant and control cell lines (HEp3 and MDA-MB-231). d) q-PCR analysis of TMEM229b mutant and control cell lines (HEp3, expression in wild-type HEp3 set to 100%). e) q-PCR analysis of C14orf142 mutant and control cell lines (HEp3, expression in wild-type HEp3 set to 100%). Insets in (d) and (e) show representative images for colonies induced by second, independent shRNAs for TMEM229b and C14orf142.

The gene targets were then prioritized based on their impact on productive cell migration in vivo according to the degree of their compact colony phenotype. This was accomplished by using an experimental metastasis approach whereby the phenotype of each clone was validated after intravenous injection into ex ovo chicken embryos and images of the resulting metastatic colonies were captured using intravital imaging. A custom Matlab-based program was developed to analyze the images of each metastatic colony using three complementary algorithms. Significant differences were not detected in the rate of proliferation of the hit clones in vitro, however, several clones were observed to grow at different speeds in vivo (FIG. 3a). Therefore to mitigate the effect of differences in proliferation between individual colonies and to get an accurate assessment of in vivo cancer cell motility, algorithms were designed to analyze two distinct parameters: A) cancer cell remoteness from the colony centroid (Linear index); B) the density of cancer cells within the metastatic colony area (Density index) and; C) the total area occupied by each metastatic colony (Area index, FIG. 3b-d). Briefly, the first algorithm creates a mask using GFP signal to delineate the cancer cells and uses a 360° line scan through the centroid to build an average line plot fitted to a Gaussian distribution. The deviation in Gaussian radial line-scan intensity distribution between colonies formed by individual clones relative to control shRNA colonies is used to generate the colony Linear index. The second and third algorithms use the fluorescence mask to measure individual metastatic colony areas (Area index) and calculate the fluorescence density within each area (Density index). For each of the clones obtained from the original screen, 10 individual colonies were analyzed and then sorted based on their Linear and Area index values. While each index produced a similar ranking of the colonies identified in the screen, several visually compact clones were poorly identified by either one or the other method alone (FIG. 3b-d). For this reason, the three algorithms were combined to create an overall colony Compactness Index (CI) that was used to stratify the phenotypes of the hit clones compared to the positive control (colonies in embryos injected with migration-blocking antibody) and the negative control (scrambled shRNA expressing HEp3 clone, FIG. 3 a-d). The CI was calculated from the Z-scores (experimental−control/SD control) for each index where C.I.=Z(Density index)−Z(Linear index)−Z(Area Index).

Figure 7:
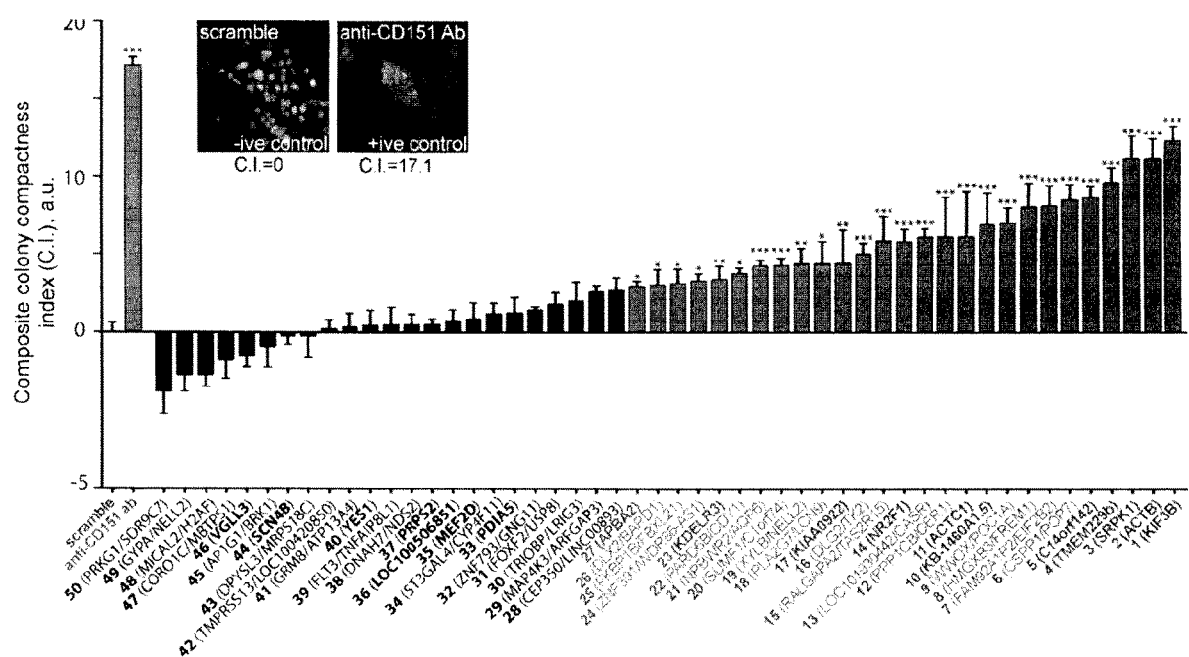
FIG. 7 is a graphical representation of the composite compactness index (CI) distribution of screen hits relative to positive (anti-CD151) and negative (scramble shRNA) controls. Screen hits that are significantly more compact than negative control are indicated in green. Clones containing a single shRNA species are in bold. For clones containing multiple shRNAs, the two most predominant shRNA are shown. Statistical significance was determined using one-way ANOVA with Fisher's LSD test (*$p<0.05$, $p, 0.01$, *$p<0.001$)

The morphology of the positive control colonies, generated after treatment with the CD151-targeted migration-blocking antibody (positive control), resulted in the most dramatic increase in the CI ($17.1 \pm 1.68$) compared to highly invasive metastatic colonies generated by negative control, scramble shRNA expressing cells (negative control, $8.515e-009 \pm 1.68$) (FIG. 3a). Statistical analysis of the CI index revealed 27 clones with metastatic colony phenotypes whose CI differed significantly ($p \leq 0.05$) from those of the negative control (FIG. 7). Eleven (11) out of these 27 clones contained single shRNAs (Kif3b, ACTB, SRPK1, TMEM229b, C14orf142, KB-1460A 1.5, ACTC1, KDELR3, APBA2, KIAA0922 and Nr2f1). Clones containing a single shRNA and CI≥5.0 were selected for downstream analysis (see Table 1).

TABLE 1

| Clone # | shRNA IDs | Function | C.I. |
|---|---|---|---|
|  | anti-CD151 ab | positive control | 17.1 ± 0.5 |
| 1 | KIF3B | Kinesin motor complex subunit, vesicle transfer | 12.4 ± 0.92 |
| 2 | ACTB | Cell cytoskeleton protein, cytoskeleton organization | 11.2 ± 01.2 |
| 3 | SRPK1 | Protein kinase, splicing regulation | 11.2 ± 01.3 |
| 4 | TMEM229B | Transmembrane protein, function unknown | 9.7 ± 0.8 |
| 5 | C14orf142 | Expressed at protein level, function unknown | 8.8 ± 0.6 |
| 10 | KB-1460A1.5 | Long non-coding RNA; Function unknown | 6.9 ± 2.0 |
| 11 | ACTC1 | Cell cytoskeleton protein; Cytoskeleton organization | 6.1 ± 2.9 |
| 14 | NR2F1 | Orphan nuclear receptor; Gene expression regulation | 5.9 ± 0.7 |
| 17 | KIAA0922 | Expressed at protein level; Function unknown | 4.4 ± 2.1 |
| 23 | KDELR3 | Endoplasmic Reticulum Receptor; Protein sorting | 3.4 ± 0.8 |
| 27 | APBA2 | Neuronal adapter protein; Vesicular trafficking | 2.9 ± 0.3 |
|  | Scramble | negative control | 0.0 ± 0.6 |

To confirm that the observed inhibition of in vivo motility was due to the shRNA-mediated depletion of the target gene(s) and not an off-target effect, independent shRNA constructs were utilized to create new HEp3 clones for Kif3b (CI=12.4), SRPK1 (CI=11.2), TMEM229b (CI=9.7), Nr2f1 (CI=5.9) and C14orf142 (CI=8.8)(FIG. 4a-e). Analysis of the gene and protein expression of each target protein in the original hit clones and the newly derived clones confirmed specific knock-down of the target proteins (FIG. 4a-e). The clones bearing independent shRNAs were then validated using an in vivo metastatic colony formation assay, and all candidate genes reproduced the compact colony phenotype with CI values similar to those of their primary screen hit clone (FIG. 4f).

Based on therapeutic relevance and potential to develop specific inhibitors, further studies were focused on Kif3b, Nr2f1 and SRPK1 genes. To gain additional insight into the migratory phenotypes created by knockdown of these genes, high-resolution in vivo time lapse imaging was performed of individual metastatic colonies and the invasive front of primary tumors derived from each clone compared to control (scrambled) shRNA transduced HEp3 cells. shRNA-mediated inhibition of each of these targets was observed to reduce both the velocity and directionality of cancer cell migration (FIG. 1a-f). Cancer cells from each of the shKif3b, shNr2f1 and shSRPK1 clones displayed either a lack of motility or unproductive migration patterns within the metastatic lesions (FIG. 1a, c-d) and at the invasive front of the primary tumor (FIG. 1b, e-f). Despite the fact that average velocity of cancer cells was higher at the invasive tumor front compared to the metastases, the number of cancer cells that escaped the tumor was decreased significantly in the shKif3b, shNr2f1 and shSRPK1 clones compared to the control (FIG. 1g). Intravital imaging of control or hit clones at the invasive front showed that while control HEp3 cells tend to form a single dominant protrusion in the direction of motility, the shKif3b, shNr2f1 and shSRPK1 clones tended to form multiple protrusions that extend in all directions in an uncoordinated fashion (FIG. 1b,h). In conclusion, this screening approach predominantly identified genes that are required for coordinating directional in vivo cell migration.

Figure 2:
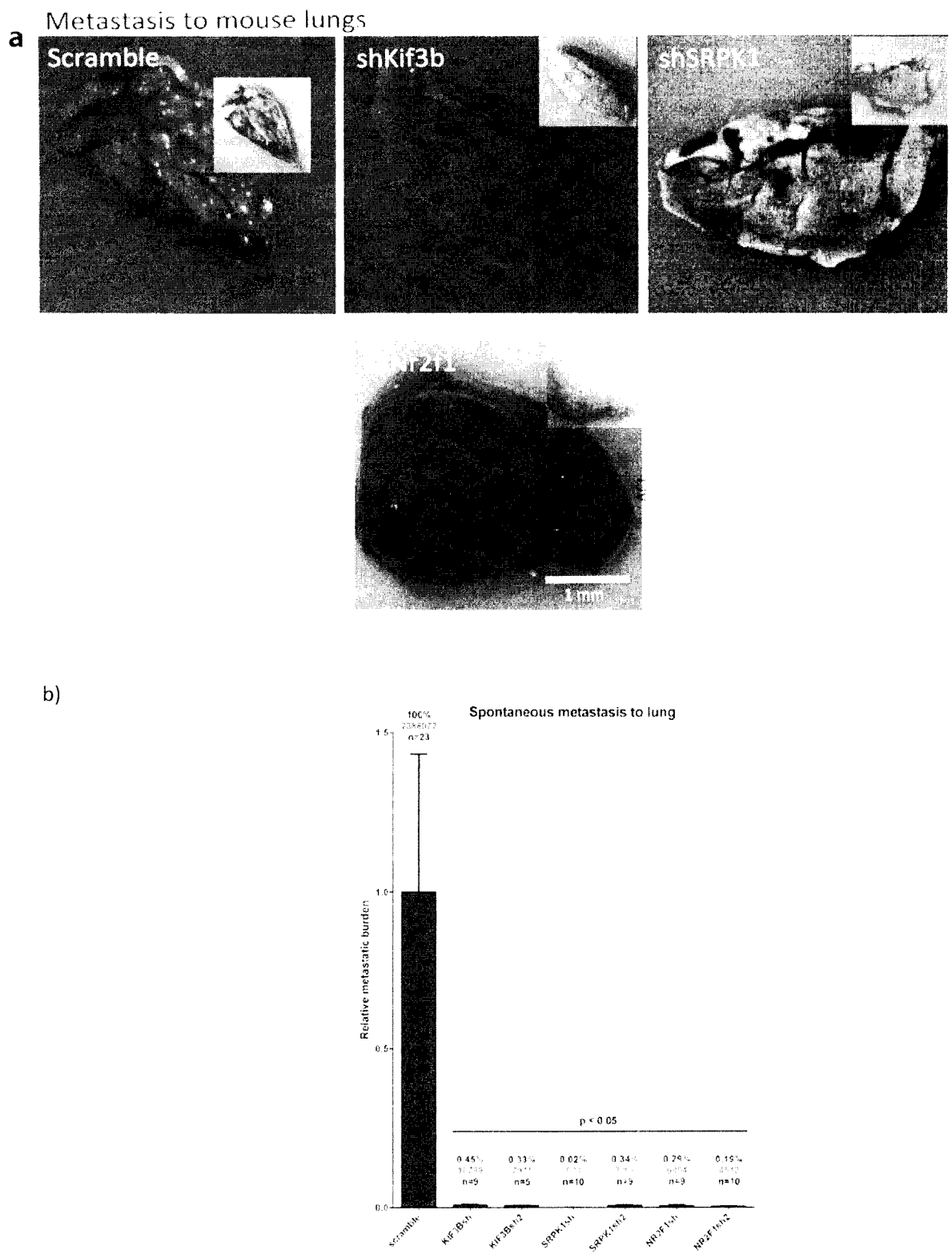
FIG. 2. is a graphical representation showing that targeting the screen identified genes blocks spontaneous cancer cell metastasis in vivo. a) Stereo-fluorescent images of the nude mice lungs that were subcutaneously injected with control (scramble) shRNA transduced HEp3 cells or HEp3 cells stably expressing shRNAs targeting Kif3b, SRPK1 and Nr2f1; b) Precise quantification of HEp3 cancer cells metastasized to lung as determined by human a/u q-PCR. Data is expressed as relative metastatic burden in percentage, and as total number of cancer cells detected (colored numbers) when estimated using a standard curve; c) Primary tumor weight of control and knockdown cell lines induced tumors used in the experiment.
Figure 2:
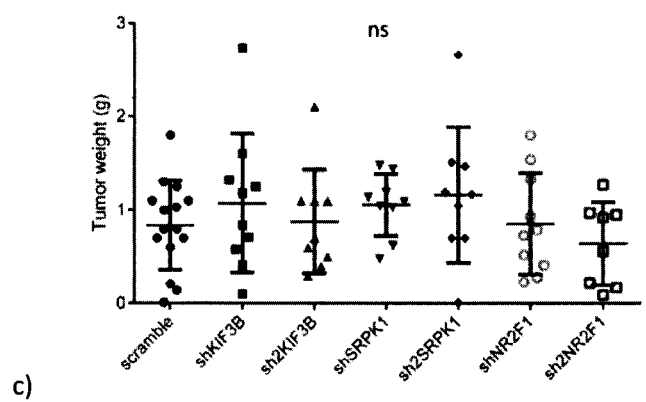

To test whether genes required for in vivo cell motility and directional cell migration would also be required for intravasation and metastasis, the hit clones were evaluated in a murine model of spontaneous metastasis to the lungs. To this end, subcutaneous HEp3 tumors were established in the flank of nude mice using parental, scrambled shRNA control or shKif3b, shNr2f1 and shSRPK1 expressing tumor cells. When the primary tumors reached 1.5 cm$^3$, the lungs were examined for the presence of metastasis using whole-mount fluorescence stereomicroscopy and then quantitatively using human a/u specific q-PCR (FIG. 2a,b). In animals bearing shRNA scramble control HEp3 tumors (n=23) significant metastasis to the lungs was detected by fluorescence imaging (FIG. 2a). In contrast, metastatic lesions were rarely observed in the lungs of animals bearing KIF3Bsh/sh2, SRPK 1sh/sh2 and NR2F 1sh/sh2 tumors, and these were very small in size (FIG. 2a). To accurately quantify the burden of metastatic HEp3 cancer cells in murine lungs, we extracted genomic DNA and performed human-specific a/u q-PCR. The precise enumeration of metastatic cells in the lung was then determined by comparing this data to a standard curve generated from HEp3 cells. The scramble shRNA control had an average of 2.4 million disseminated cancer cells per lung. In contrast, animals bearing KIF3Bsh/sh2, SRPK 1sh/sh2 and NR2F1sh/sh2 tumors had a dramatic inhibition of metastatic dissemination, with reductions in metastasis to the lungs of 99.55% and 99.67% respectively for KIF3Bsh and Sh2, 99.98% and 99.66% respectively for SRPK1 sh and sh2, and 99.71% and 99.81%, respectively for NR2F1sh and sh2 (FIG. 2b). There was no significant difference in primary tumor weights between the control and hit shRNA clone tumors at the time of sacrifice (FIG. 2c). These results confirm that Kif3b, Nr2f1 and shSRPK1 are each required both for in vivo cancer cell motility and for successful spontaneous metastasis, and therefore represent highly promising therapeutic targets for metastasis.

Figure 5:
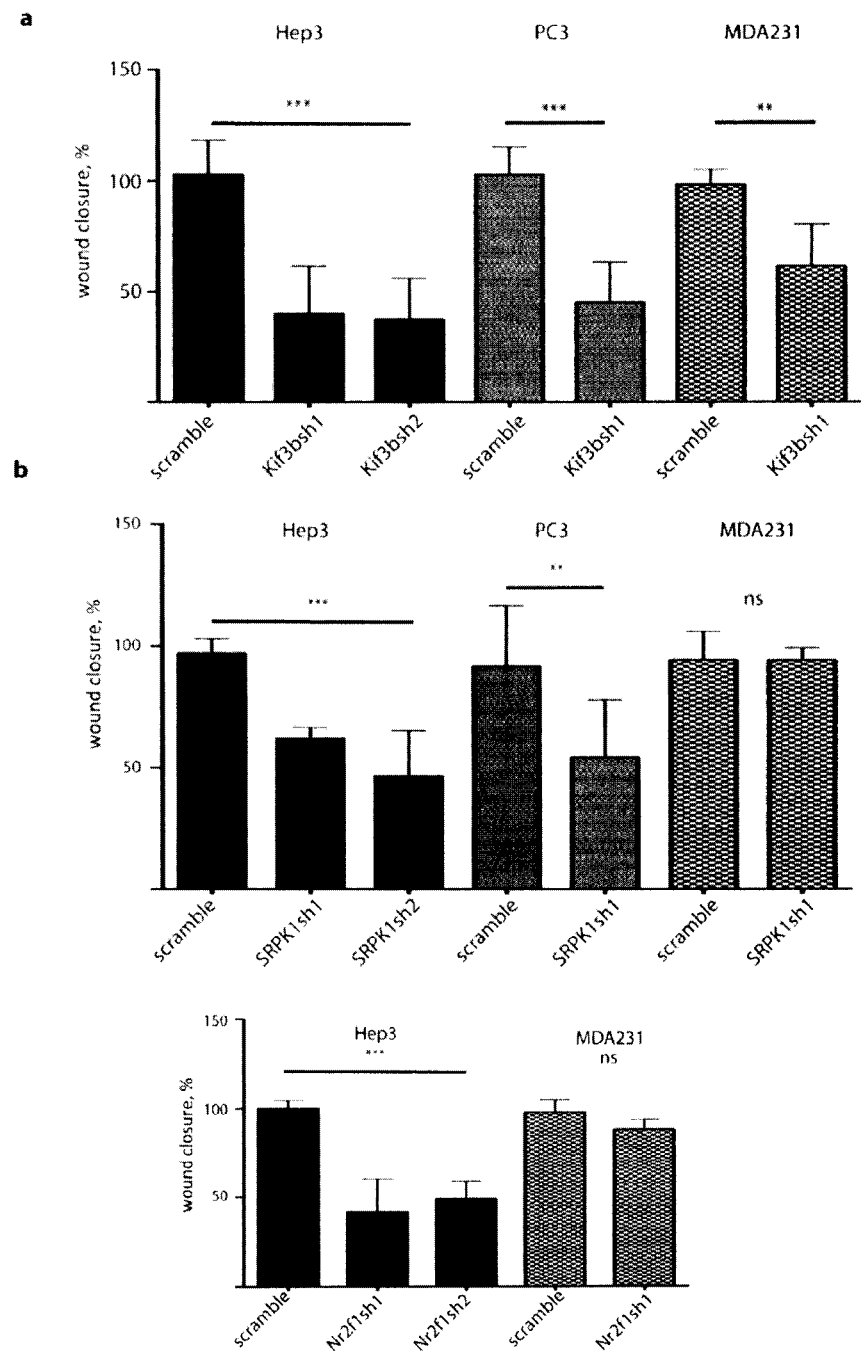
FIG. 5. is a graphical representation showing effect of the Kif3b and SRPK1 expression knockdown on the in vitro cancer cell migration. Modified cell scratch assay that utilizes magnetically attachable stencils, Mats was used ref a) Mats (magnetically attachable stencils) in vitro migration assay of control and mutant Kif3b cell lines. b) Mats in vitro migration assay of control and mutant SRPK1 cell lines. For each cell line average value for wild type was set at 100%.

Considering the possibility that the observed motility phenotypes could be specific to the highly metastatic human epidermoid-carcinoma cell line HEp3, the hits: Kif3b, SRPK1 and Nr2f1 were silenced in two additional cell lines representing two distinct types of epithelial human cancer: MDA-MB-231 (breast cancer) and PC3 (prostate cancer). Silencing of Kif3b expression efficiently blocked in vitro cell migration in all of the cancer cell lines (FIG. 5a). Interestingly, silencing SRPK1 significantly inhibited the motility of HEp3 and PC3 cells in vitro but had no effect on the in vitro motility of MDA-MB-231 (FIG. 5b). Finally, silencing of Nr2f1 inhibited HEp3 migration in vitro but had no effect on MDA-MB-231. No Nr2f1 expression was detected in PC3 cells (FIG. 5c). This may explain the fact why these genes have not been detected in previous in vitro screens. Indeed, SRPK1 and Nr2f1 would not be detected if MDA-MB-231 cells were used to perform the screen.

Figure 8:
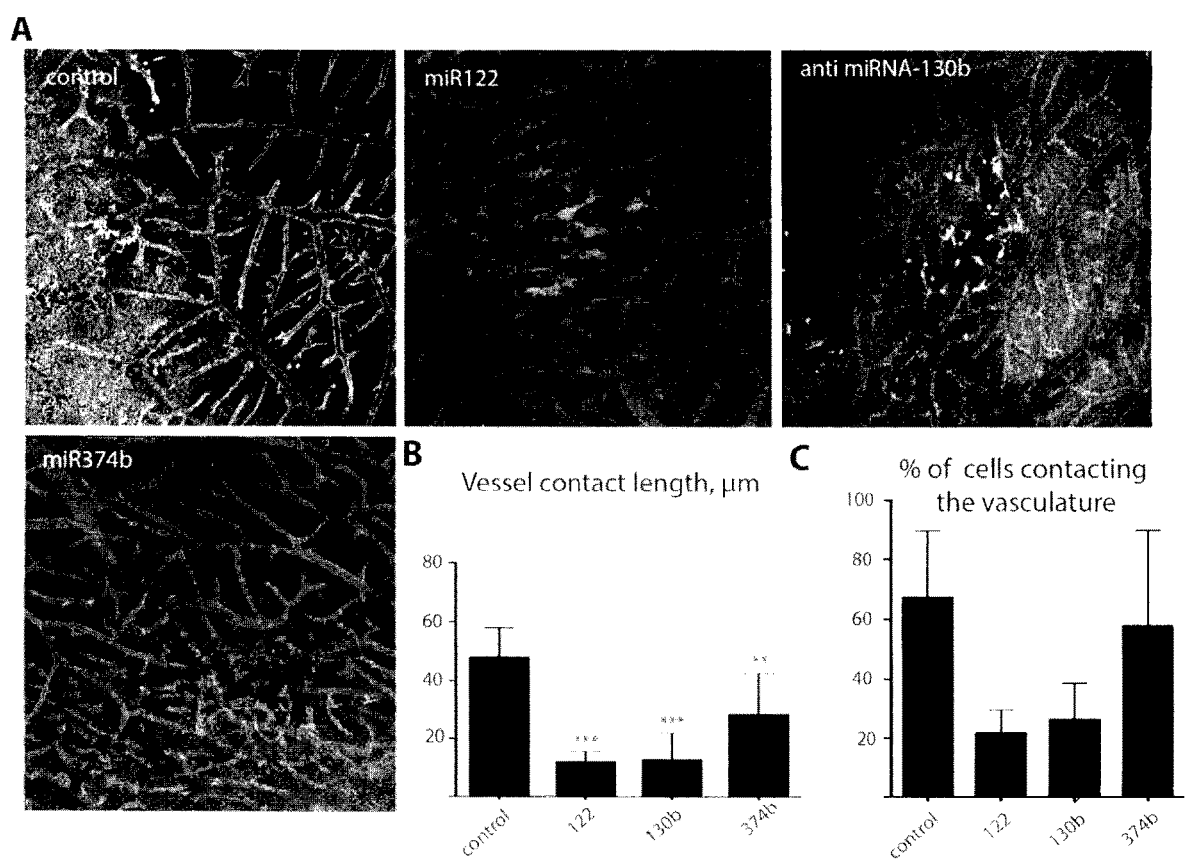
FIG. 8. is a graphical representation showing that elevated expression of screen identified miRNAs blocks invasive metastatic lesion formation. a) Metastatic lesions formed by cancer cells that express control, miR122, miR374b or anti-miRNA-130b constructs. b) Quantification of cancer cell-vessel contact length for metastatic lesions formed by cancer cells that express control, miR122, miR374b or anti-miRNA-130b constructs. c) Quantification of percentage of vessel contacting cancer cells for metastatic lesions formed by cancer cells that express control, miR122, miR374b or anti-miRNA-130b constructs.

Validation of the miRNA 130b and miRNA 122 clones by independent miRNA constructs confirmed their non-invasive phenotype (FIG. 8A). Significantly, HT1080 cells that were engineered to overexpress miRNA-122 or miRNA-130b inhibitor formed compact metastatic colonies that displayed less prominent contacts with chicken CAM vasculature (FIG. 8B, C).

Figure 9:
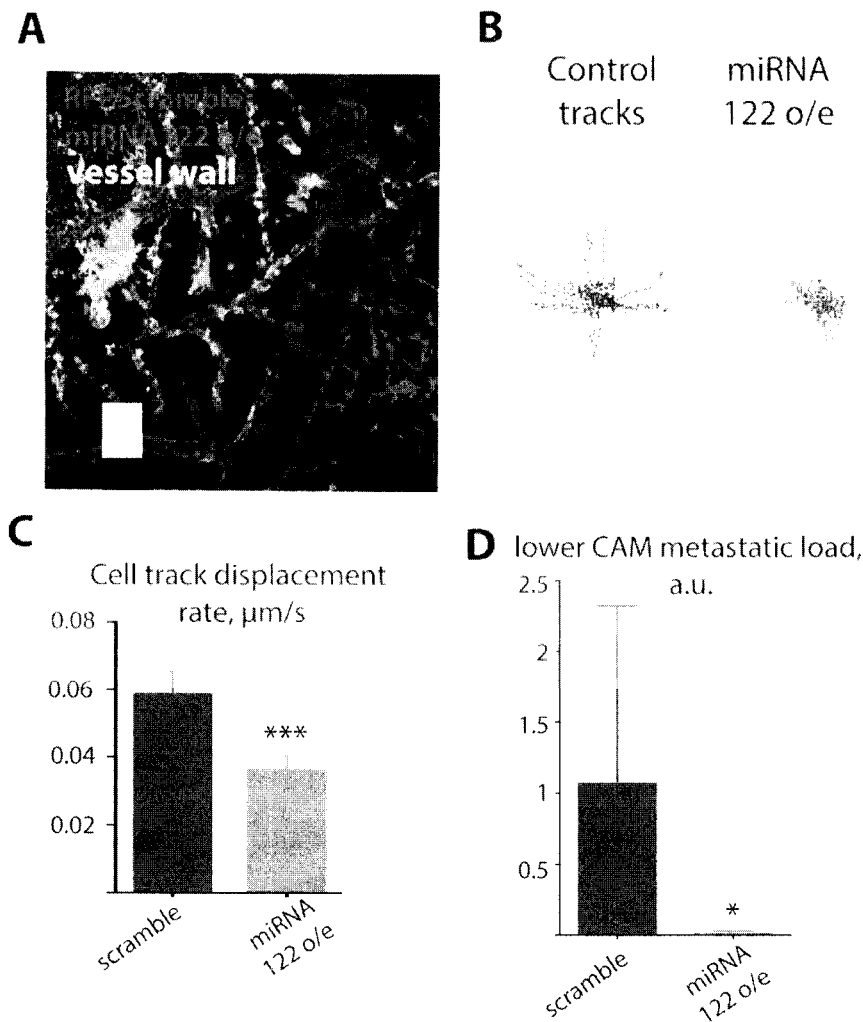
FIG. 9. is a graphical representation showing that elevated expression of screen identified miRNAs blocks cancer cell invasion. a) Metastatic lesions formed by cancer cells that express control (red) or miR122 (green) overexpressing cells. b) Cell migration tracks for cancer cells that express control (red) or miR122 (green) overexpressing cells c) Quantification of cancer cell displacement rates that express control (red) or miR122 o/e constructs. d) Quantification of metastatic load (spontaneous metastasis) of control (red) or miR122 o/e cancer cells (green).
Figure 10:
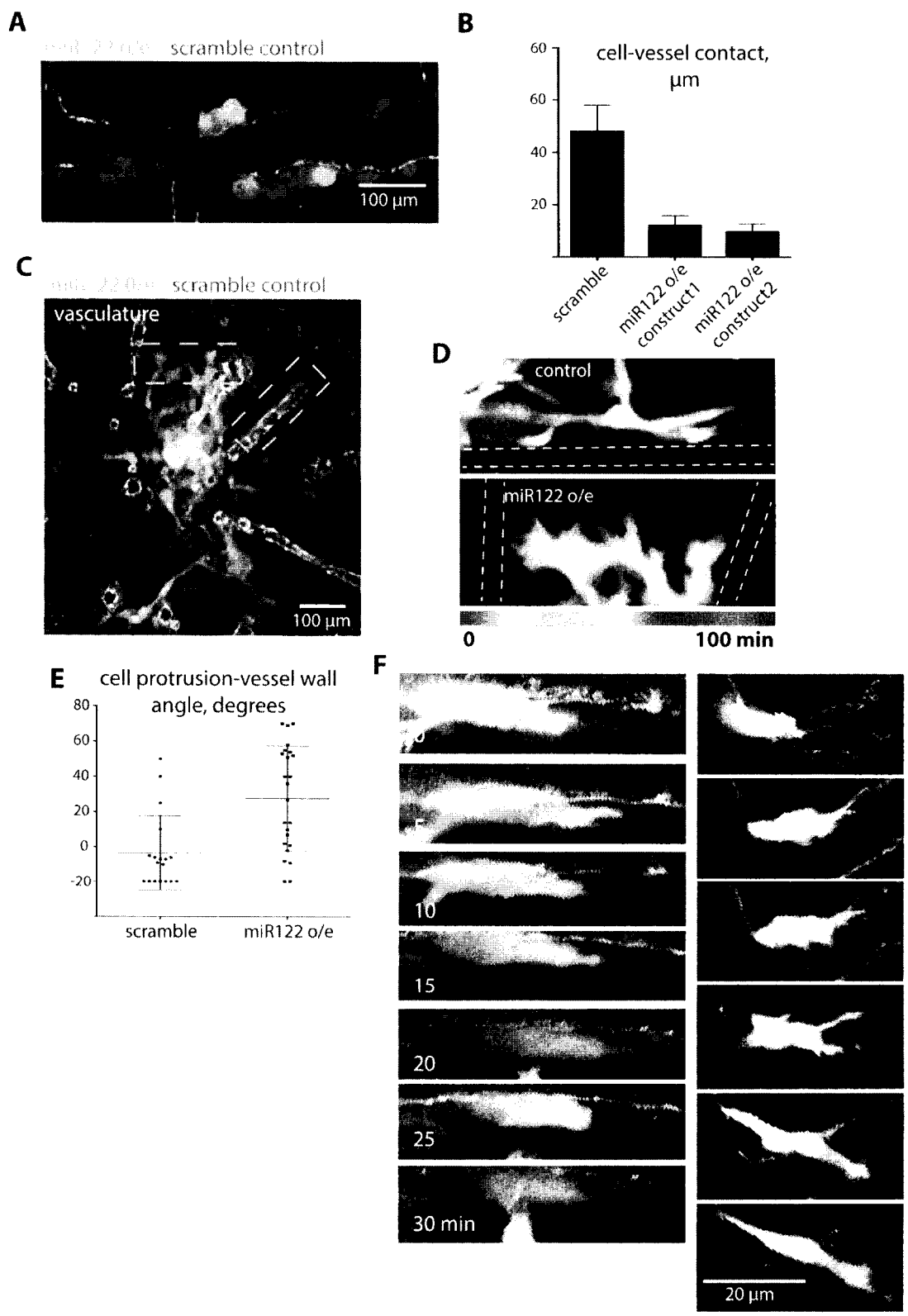
FIG. 10. is a graphical representation showing that elevated expression of screen identified miRNAs blocks cancer cell invasion along the vasculature. a) Scramble control (red) or miR122 (green) overexpressing cells next to the blood vessel wall. b) Cancer cell-blood vessel contacts for or miR122 o/e overexpressing cells (two independent constructs) c-d) Color-coded representation of control and miR122 o/e cancer cell protrusion along the vasculature. e) Quantification of cancer cell protrusion-vessel wall angle for control and miR122 o/e cancer cells. f) Imaging of control and miR122 o/e cancer cell interaction with blood vessel oriented collagen fibers (SHG).
Figure 11:
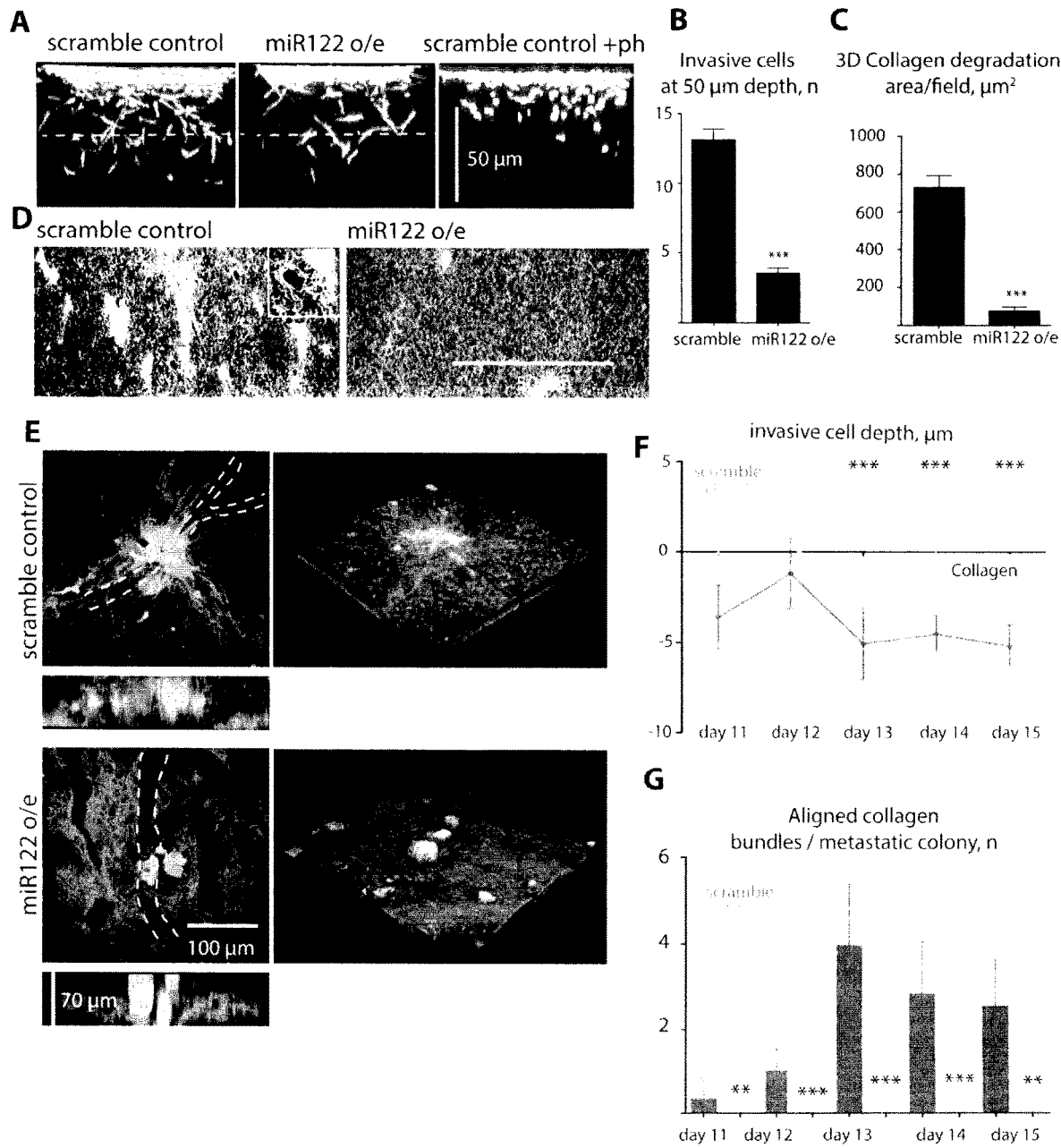
FIG. 11. is a graphical representation showing that elevated expression of screen identified miRNAs blocks cancer cell invasion into collagen matrixes. a) Invasion of scramble control, miR122 overexpressing or MT1-MMP inhibitor (phenantrione, ph) treated cells into 3D collagen matrix (rat tail collagen gel). b-c) Quantification of cancer cell invasion into the collagen matrix and collagen degradation d) Representative optical sections from (a) showing collagen degradation by control or miR122 o/e cells. e) Representative images 2D and 3D of control and miR122 o/e cancer cells in the chicken CAM collagen matrix (SHG). Note that miR122 o/e cells fail to invade into the collagen and grow on the surface (lower panel). f) Quantification of metastatic colony depth for control and miR122 o/e cells days 1-5 post cancer cell injection. g) Quantification of aligned collagen bundles for control and miR122 o/e cells days 1-5 post cancer cell injection.
Figure 12:
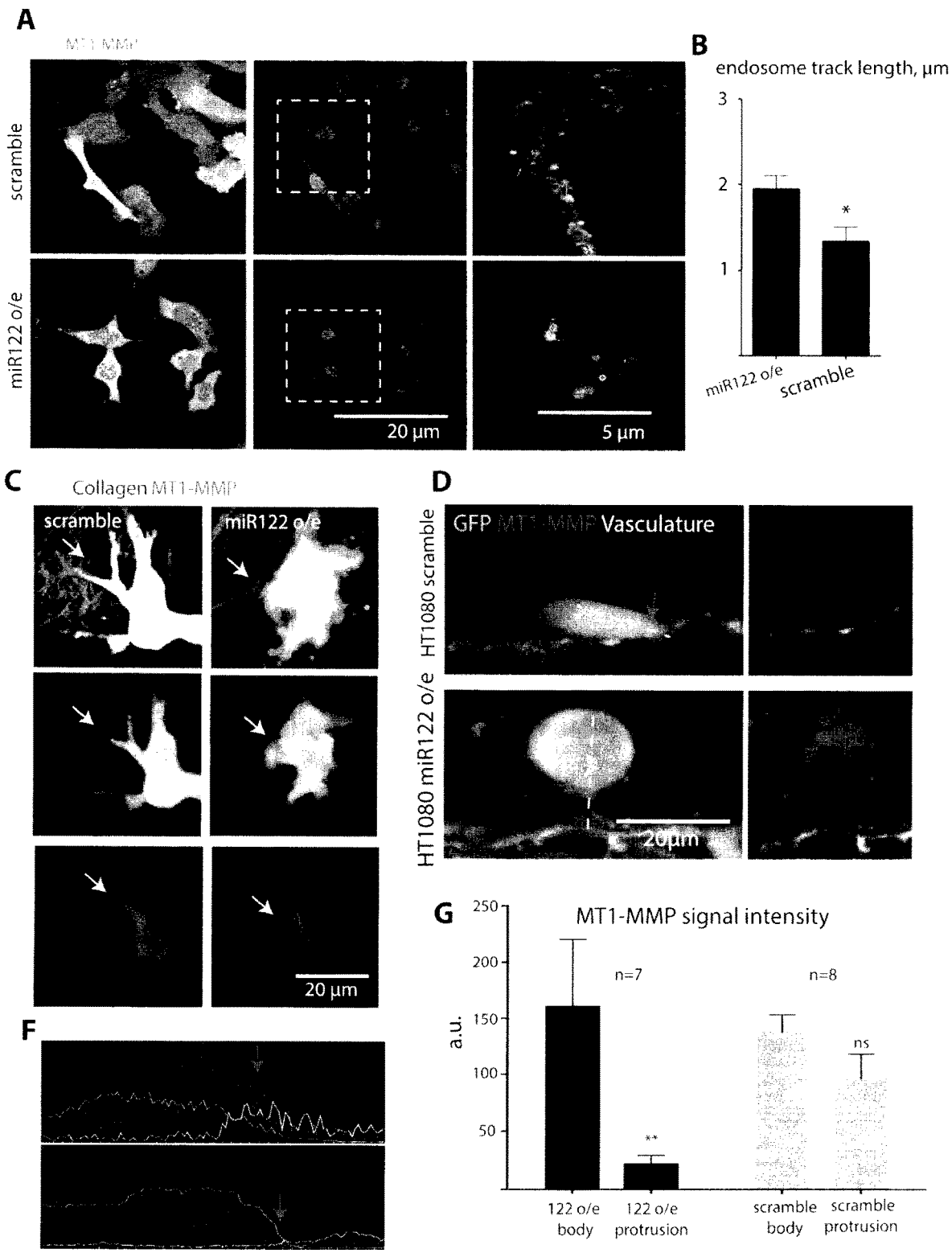
FIG. 12. is a graphical representation showing that elevated expression of screen identified miRNAs blocks normal MT1-MMP trafficking and localization. a) Representative images showing MT1-MMP vesicle localization and trajectories in control and miR122 o/e cells. b) Quantification of MT1-MMP vesicle track length in control and miR122 o/e cancer cells. c) Representative images of control and miR122 o/e cancer cells in the chicken CAM collagen matrix (SHG). Note that miR122 o/e cells fail to properly localize MT1-MMP into the collagen contacting protrusions. d) Representative images of control and miR122 o/e cancer vessel contacting cells in the chicken CAM. Note that miR122 o/e cells fail to properly localize MT1-MMP to the cancer cell-vessel wall contact areas. f) Signal intensity line scans for images in (d) that were done along the dashed lines. Red arrows point to the cancer cell-blood vessel wall contacts. g) Quantification of MT1-MMP signal intensity in protrusions for control and miR122 o/e cancer cells.
Figure 13:
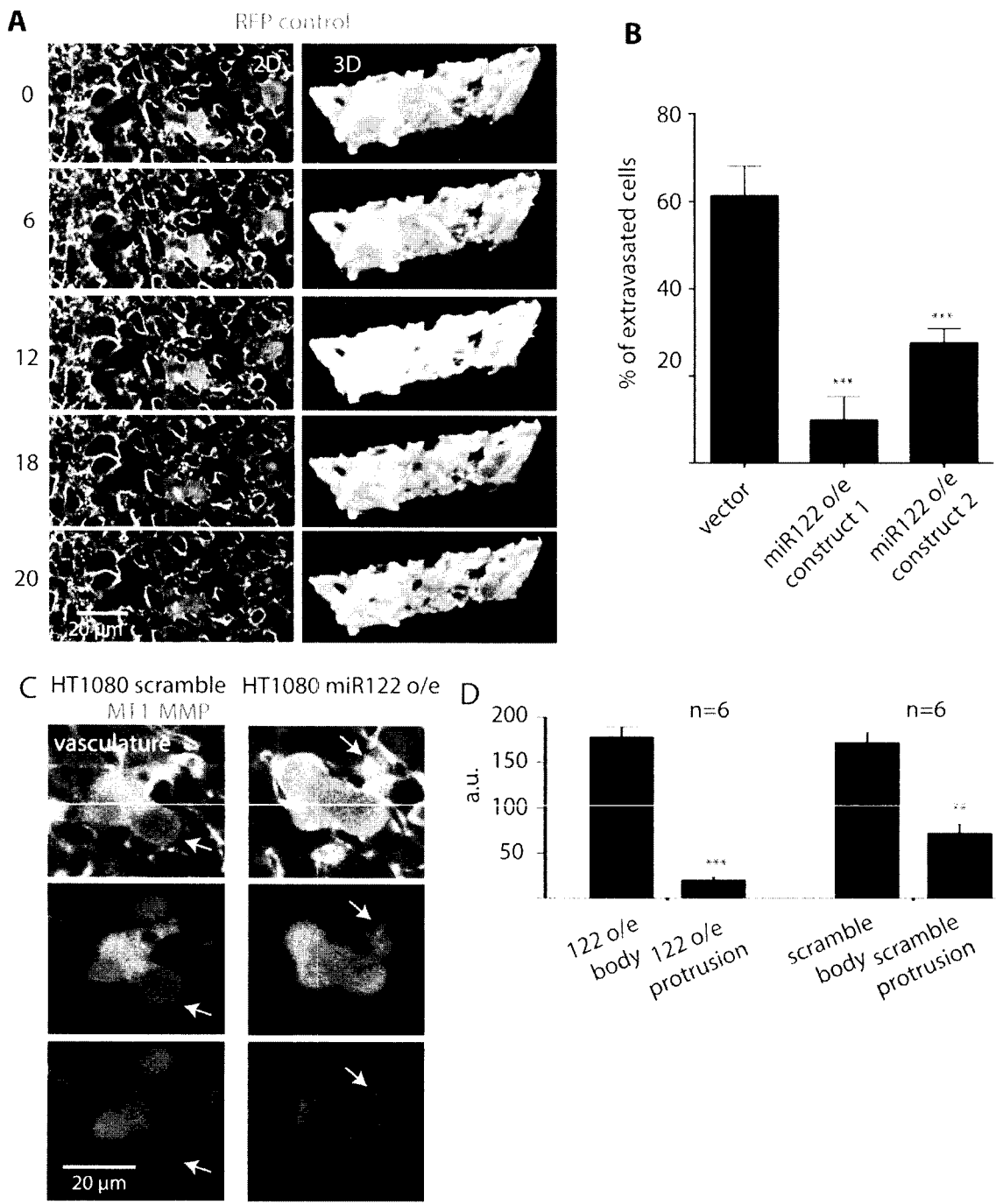
FIG. 13. is a graphical representation showing that elevated expression of screen identified miRNAs blocks cancer cell extravasation. a) Representative images showing control (red) and miR122 o/e (green) cells extravasating out of the chicken CAM vasculature. b) Quantification of control and miR122 o/e cancer cell extravasation. c) Representative images of extravasating control and miR122 o/e cancer cells (MT1-MMP overexpressing, red) in the chicken CAM vasculature. Note that miR122 o/e cells fail to properly localize MT1-MMP into the vessel wall contacting protrusions. d) Quantification of MT1-MMP signal intensity in protrusions for control and miR122 o/e cancer cells.

To gain further insight into the mechanisms by which the miRNAs identified in the screen block the invasive migration of cancer cells in vivo, intravital imaging experiments were performed with the primary focus being on the effect of miRNA 122 overexpression on cancer cell invasion and metastasis. Control (RFP) cells were found to be robustly invaded within the CAM tissue, preferentially tracking along pre-existing blood vessels (FIGS. 9A-C and FIGS. 2A-C). Moreover, control, scramble vector transduced cells actively metastasized in chicken CAM in ovo metastasis model while miRNA 122 overexpressing cells failed to do so (FIG. 9F). Co-injection of differentially labeled control, scramble vector expressing cells (RFP) and miRNA 122 overexpressing cells (GFP) followed by high-resolution intravital imaging revealed that control cells preferentially protrude and invade along the vasculature, forming distinct contacts with perivascular collagen fibers while miRNA 122 overexpressing cells protrude and invade independently of vasculature and do not form contacts with perivascular collagen (FIG. 10A-F). Chicken CAM represents a collagen rich membrane that is penetrated by the vasculature. Metastatic cancer cells invading collagen rich matrixes via a) moving along pre-existing collagen fiber bundles; and b) locally degrading and reorganizing collagen matrix, creating aligned bundles of collagen that are later used for directional cancer cell invasion. Indeed, miR122-overexpressing cells failed to invade into artificial 3D collagen matrixes. 3D collagen invasion was also blocked by MMP inhibitor phenanthroline confirming that this process is protease dependent (FIG. 11A, B). miRNA 122 overexpressing cells were invading and degrading collagen matrix significantly less than control cells as displayed by almost complete absence of areas of collagen degradation within the 3D collage matrix (FIG. 11C, D). When injected intravascularly into chicken CAM scramble transduced cells remained within the collagen matrix actively creating directional collagen bundles in their vicinity (FIG. 11E-G). In contrast, miRNA 122 cells were unable to remain deep within the collagen matrix virtually growing on the CAM surface showing little or no collagen rearrangement (FIG. 11E-G). Invasion and rearrangement of collagen rich matrixes requires their focal proteolytic degradation by cancer cell associated proteases. MT1-MMP is a key matrix-degrading enzyme which activity and localization had been shown to be important for efficient cancer cell invasion. Therefore, MT1-MMP trafficking and localization in control, scramble and miR122 overexpressing HT1080 cells was investigated. First, it was found that in in vitro culture miRNA 122 overexpressing cells display impaired MT1-MMP transport with enlarged MT1-MMP positive vesicles that display significantly shorter tracks (FIG. 12A, B). High resolution in vivo imaging showed that in control HT1080 cells MT1-MMP was localized to the sites of cancer cell protrusion-collagen fiber contacts while in miRNA 122 overexpressing cells MT1-MMP was showing mainly cytoplasmic localization (FIG. 12C). Moreover, in the perivascular control cells MT1-MMP was localized to cancer cell-vascular wall contacts while in miRNA 122 overexpressing cells MT1-MMP showed no specific localization (FIG. 12D-G). Next, miRNA 122 mediated MT1-MMP trafficking was investigated to determine whether it is required for the process of cancer cell extravasation. It was found that miRNA 122 overexpressing cells are extravasating significantly less efficiently than control, scramble infected HT1080 cells (FIG. 13A, B). Importantly, while in control cells MT1-MMP was showing distinct localization to the vascular wall breaching protrusions (invadopodia) in miRNA 122 overexpressing cells MT1-MMP was depleted from the protrusions (FIG. 13C, D).

Figure 6:
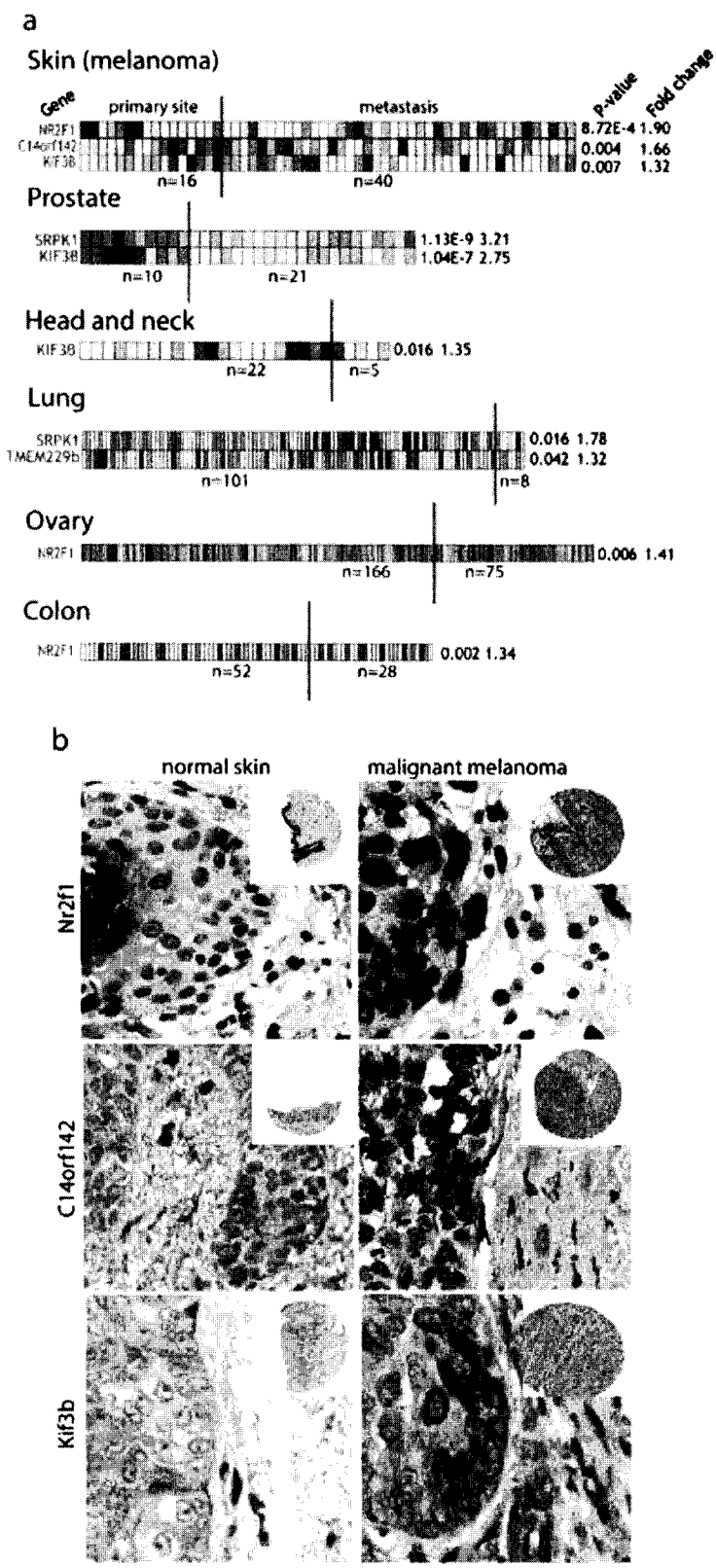
FIG. 6. is a graphical representation showing that elevated expression of screen identified genes correlates with cancer cell metastatic behavior in major types of human cancers. a) Expression of selected screen hits in the metastatic lesions versus primary tumors in skin, prostate, head and neck, lung, ovary and colon cancers (Oncomine). b) Immunohistochemical analysis Nr2f1, C14orf142 and Kif3b expression in skin (melanoma) cancer. c) Immunohistochemical analysis of SRPK1 and Kif3b expression in prostate cancer. d) Immunohistochemical analysis of Kif3b expression in head and neck (squamous cell carcinoma) cancer. e) Immunohistochemical analysis of SRPK1 and TMEM229b expression in lung cancer. f) Immunohistochemical analysis of Nr2f1 expression in ovarian cancer. g) Immunohistochemical analysis of Nr2f1 expression in colon cancer. Red arrows point to invasive tumor fronts.
Figure 6:
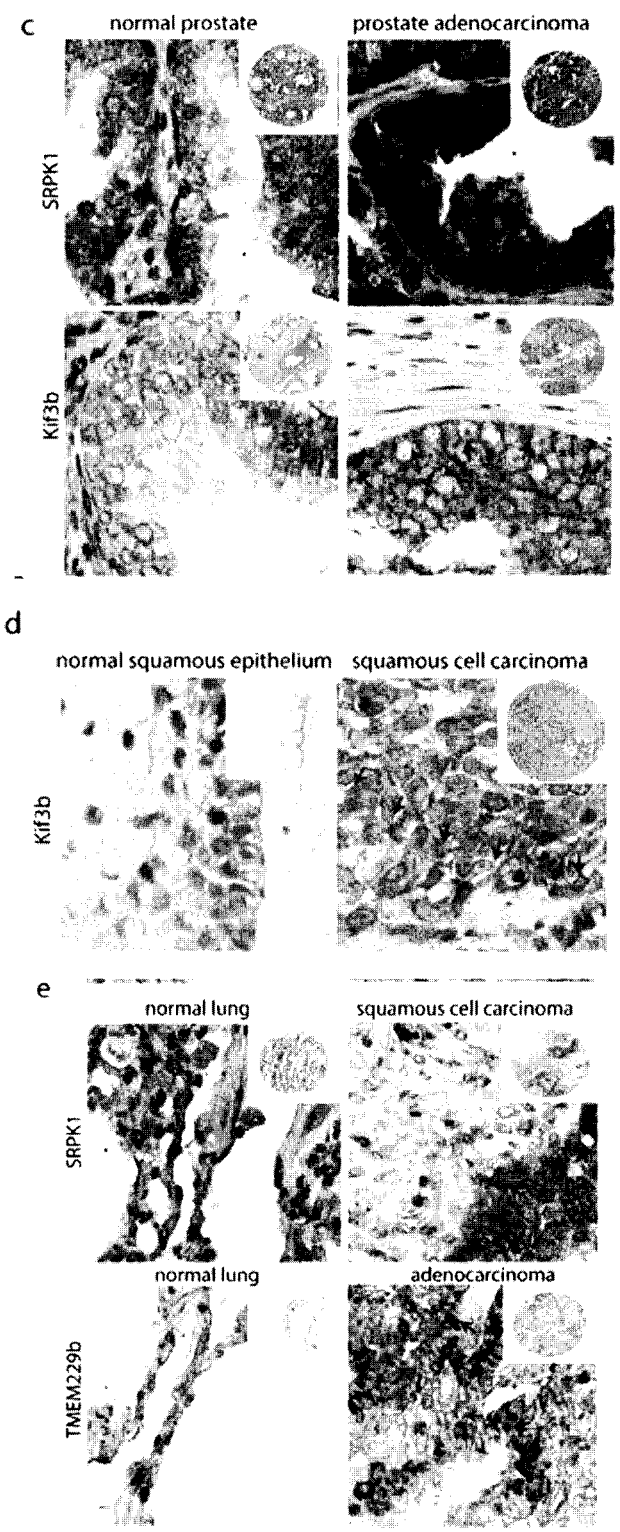
Figure 6:
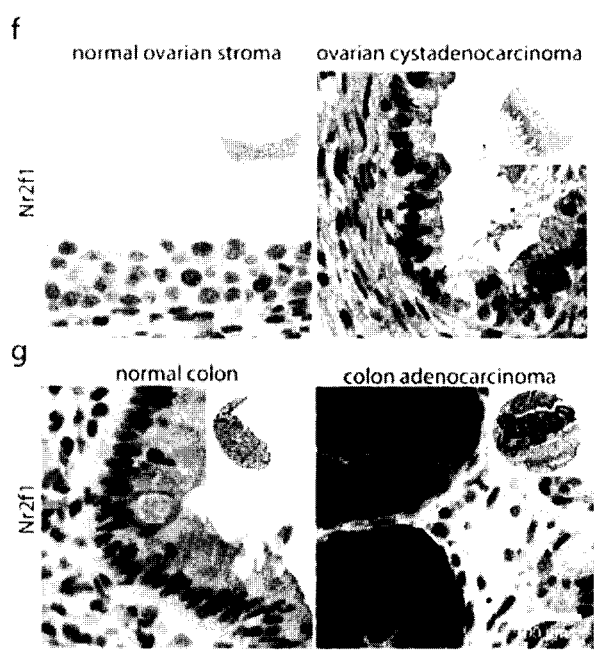

Having identified several promising metastasis therapeutic targets in cancer cell lines, the potential relevance of these genes for human cancer progression and metastasis was investigated. To do this, the Oncomine collection of human cancer gene expression databases (Rhodes et al., Neoplasia 9:166-180, 2007) was queried to determine whether their expression is associated with metastasis or poor clinical outcomes. Indeed, the analysis indicated that the top hit genes identified in the screen are significantly upregulated in metastatic lesions of several solid cancer types including: melanoma (Nr2f1, C14orf142 and Kif3b), prostate (SRPK1 and Kif3b), head and neck (Kif3b), lung (SRPK1 and TMEM229b), ovarian (Nr2f1) and colon (Nr2f1) (FIG. 6a). Moreover, a detailed survey of immunohistochemical staining of human cancers in the human Protein Atlas database showed that SRPK1, Kif3b, Nr2f1, C14orf142 and TMEM229b all display significantly increased expression in the invasive zone of the primary tumors of these cancers as delineated by a Cancer Pathologist (FIG. 6b-g).

In summary, quantitative in vivo approach was used that allows for discovery of anti-metastatic therapeutic targets. The rapid and quantitative nature of this assay allowed for efficient filtering through a vast number of initial candidate genes and lead to the discovery of several new anti-metastatic targets. The anti-metastatic targets identified using this screening approach have no or little effect on the cancer cell ability to migrate in vitro.

The invention claimed is:

1. A method for inhibiting cancer metastasis in a subject, comprising administering an effective amount of an inhibitor of C14orf142 to the subject, wherein the inhibitor is a gene silencing nucleic acid molecule.

2. The method of claim 1, wherein the gene silencing nucleic acid molecule is an short interfering RNA, antisense oligonucleotide, short hairpin RNA, microRNA, ribozyme or other RNA interference molecule.

\* \* \* \* \*